(12) United States Patent  
Antwiler

(10) Patent No.: US 8,785,181 B2  
(45) Date of Patent: *Jul. 22, 2014

(54) CELL EXPANSION SYSTEM AND METHODS OF USE

(71) Applicant: Terumo BCT, Inc., Lakewood, CO (US)

(72) Inventor: Glen Delbert Antwiler, Lakewood, CO (US)

(73) Assignee: Terumo BCT, Inc., Lakewood, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/653,268

(22) Filed: Oct. 16, 2012

(65) Prior Publication Data

US 2013/0102070 A1 Apr. 25, 2013

Related U.S. Application Data

(62) Division of application No. 12/042,798, filed on Mar. 5, 2008, now Pat. No. 8,309,347.

(60) Provisional application No. 60/892,908, filed on Mar. 5, 2007, provisional application No. 60/892,911, filed on Mar. 5, 2007, provisional application No. 60/892,966, filed on Mar. 5, 2007, provisional application No. 60/892,977, filed on Mar. 5, 2007, provisional application No. 60/911,393, filed on Apr. 12, 2007, provisional application No. 60/911,594, filed on Apr. 13, 2007, provisional application No. 60/971,494, filed on Sep. 11, 2007.

(51) Int. Cl.
| | | |
|---|---|---|
| *C12M 3/00* | (2006.01) | |
| *C12M 1/00* | (2006.01) | |
| *C12N 5/02* | (2006.01) | |
| *C12M 1/12* | (2006.01) | |

(52) U.S. Cl.  
USPC ............ 435/293.1; 435/289.1; 435/394; 435/297.5

(58) Field of Classification Search  
None  
See application file for complete search history.

(56) References Cited

U.S. PATENT DOCUMENTS

| | | |
|---|---|---|
| 3,821,087 A | 6/1974 | Knazek et al. |
| 3,896,061 A | 7/1975 | Tanzawa et al. |

(Continued)

FOREIGN PATENT DOCUMENTS

| | | |
|---|---|---|
| EP | 0220650 A2 | 5/1987 |
| JP | 2003510068 | 3/2003 |

(Continued)

OTHER PUBLICATIONS

Chang et al., "Membrane Bioreactors: Present and Prospects", Advances in Biochemical Engineering, 1991, pp. 27-64, vol. 44.

(Continued)

*Primary Examiner* — Anne Gussow  
*Assistant Examiner* — Reza Ghafoorian  
(74) *Attorney, Agent, or Firm* — Elizabeth J. Reagan; John R. Merkling; René A. Pereyra

(57) ABSTRACT

Cell expansion systems and methods of use are provided. The cell expansion systems generally include a hollow fiber cell growth chamber, and first and second circulation loops (intracapillary loops and extracapillary loops) associated with the interior of the hollow fibers and exterior of the hollow fibers, respectively. Detachable flow circuits and methods of expanding cells are also provided.

9 Claims, 27 Drawing Sheets

(56) References Cited

U.S. PATENT DOCUMENTS

| | | |
|---|---|---|
| 4,391,912 A | 7/1983 | Yoshida et al. |
| 4,439,322 A | 3/1984 | Sonoda et al. |
| 4,647,539 A | 3/1987 | Bach |
| 4,650,766 A | 3/1987 | Harm et al. |
| 4,722,902 A | 2/1988 | Harm et al. |
| 4,804,628 A | 2/1989 | Cracauer et al. |
| 4,885,087 A * | 12/1989 | Kopf .................... 210/321.72 |
| 4,889,812 A | 12/1989 | Guinn et al. |
| 4,894,342 A | 1/1990 | Guinn et al. |
| 4,918,019 A | 4/1990 | Guinn |
| 4,973,558 A | 11/1990 | Wilson et al. |
| 5,079,168 A | 1/1992 | Amiot |
| 5,126,238 A | 6/1992 | Gebhard et al. |
| 5,162,225 A | 11/1992 | Sager et al. |
| 5,202,254 A | 4/1993 | Amiot |
| 5,330,915 A | 7/1994 | Wilson et al. |
| 5,399,493 A | 3/1995 | Emerson et al. |
| 5,416,022 A | 5/1995 | Amiot |
| 5,437,994 A | 8/1995 | Emerson et al. |
| 5,459,069 A | 10/1995 | Palsson et al. |
| 5,510,257 A | 4/1996 | Sirkar et al. |
| 5,541,105 A | 7/1996 | Melink et al. |
| 5,605,822 A | 2/1997 | Emerson et al. |
| 5,622,857 A | 4/1997 | Goffe |
| 5,631,006 A | 5/1997 | Melink et al. |
| 5,635,386 A | 6/1997 | Palsson et al. |
| 5,635,387 A | 6/1997 | Fei et al. |
| 5,646,043 A | 7/1997 | Emerson et al. |
| 5,656,421 A | 8/1997 | Gebhard et al. |
| 5,670,147 A | 9/1997 | Emerson et al. |
| 5,670,351 A | 9/1997 | Emerson et al. |
| 5,688,687 A | 11/1997 | Palsson et al. |
| 5,763,194 A | 6/1998 | Slowiaczek et al. |
| 5,763,261 A | 6/1998 | Gruenberg |
| 5,763,266 A | 6/1998 | Palsson et al. |
| 5,882,918 A | 3/1999 | Goffe |
| 5,888,807 A | 3/1999 | Palsson et al. |
| 5,958,763 A | 9/1999 | Goffe |
| 5,981,211 A | 11/1999 | Hu et al. |
| 5,985,653 A | 11/1999 | Armstrong et al. |
| 5,994,129 A | 11/1999 | Armstrong et al. |
| 5,998,184 A | 12/1999 | Shi |
| 6,001,585 A | 12/1999 | Gramer |
| 6,048,721 A | 4/2000 | Armstrong et al. |
| 6,096,532 A | 8/2000 | Armstrong et al. |
| 6,228,635 B1 | 5/2001 | Armstrong et al. |
| 6,238,908 B1 | 5/2001 | Armstrong et al. |
| 6,326,198 B1 | 12/2001 | Emerson et al. |
| 6,566,126 B2 | 5/2003 | Cadwell |
| 6,582,955 B2 | 6/2003 | Martinez et al. |
| 6,616,912 B2 | 9/2003 | Eddleman et al. |
| 6,642,019 B1 | 11/2003 | Anderson et al. |
| 6,667,034 B2 | 12/2003 | Palsson et al. |
| 6,835,566 B2 | 12/2004 | Smith et al. |
| 6,844,187 B1 | 1/2005 | Weschler et al. |
| 6,943,008 B1 | 9/2005 | Ma |
| 6,969,308 B2 | 11/2005 | Doi et al. |
| 6,979,308 B1 | 12/2005 | MacDonald et al. |
| 7,033,823 B2 | 4/2006 | Chang |
| 7,041,493 B2 | 5/2006 | Rao |
| 7,112,441 B2 | 9/2006 | Uemura et al. |
| 7,172,696 B1 | 2/2007 | Martinez et al. |
| 7,270,996 B2 | 9/2007 | Cannon et al. |
| 7,531,351 B2 | 5/2009 | Marx et al. |
| 7,682,822 B2 | 3/2010 | Noll et al. |
| 7,718,430 B2 | 5/2010 | Antwiler |
| 8,309,347 B2 | 11/2012 | Antwiler |
| 2007/0122904 A1 | 5/2007 | Nordon |
| 2007/0160583 A1 | 7/2007 | Lange et al. |
| 2007/0298497 A1 | 12/2007 | Antwiler |
| 2008/0220522 A1 | 9/2008 | Antwiler |
| 2008/0220523 A1 | 9/2008 | Antwiler |
| 2008/0227190 A1 | 9/2008 | Antwiler |
| 2008/0248572 A1 | 10/2008 | Antwiler |
| 2008/0254533 A1 | 10/2008 | Antwiler |

FOREIGN PATENT DOCUMENTS

| | | | |
|---|---|---|---|
| WO | 86/02379 A1 | 4/1986 | |
| WO | 88/01643 A1 | 3/1988 | |
| WO | 90/02171 A1 | 3/1990 | |
| WO | 91/07485 A1 | 5/1991 | |
| WO | 95/04813 A1 | 2/1995 | |
| WO | 95/21911 A1 | 8/1995 | |
| WO | 97/16527 A1 | 5/1997 | |
| WO | 98/53046 A1 | 11/1998 | |
| WO | 00/75275 A2 | 12/2000 | |
| WO | 01/23520 A1 | 4/2001 | |
| WO | WO 02/28996 * | 4/2002 | ............... C12M 3/06 |
| WO | 03/105663 A2 | 12/2003 | |
| WO | 2004/090112 A2 | 10/2004 | |
| WO | 2005087915 A2 | 9/2005 | |
| WO | 2007/136821 A1 | 11/2007 | |
| WO | 2007/139742 A1 | 12/2007 | |
| WO | 2007/139746 A1 | 12/2007 | |
| WO | 2007/139747 A1 | 12/2007 | |
| WO | 2007/139748 A2 | 12/2007 | |
| WO | WO 2007/139746 * | 12/2007 | ............... F16K 7/06 |

OTHER PUBLICATIONS

Chang, Ho Nam, "Membrane Bioreactors: Engineering Aspects", Biotech. Adv., 1987, pp. 129-145, vol. 5.

Eddington, Stephen M., "New Horizons for Stem-Cell Bioreactors", Biotechnology, Oct. 1992, pp. 1099-1106, vol. 10.

Gastens et al., "Good Manufacturing Practice-Compliant Expansion of Marrow-Derived Stem and Progenitor Cells for Cell Therapy", Cell Transplantation, 2007, pp. 685-696, vol. 16.

Gramer et al., "Screening Tool for Hollow-Fiber Bioreactor Process Development", Biotechnol. Prog., 1998, pp. 203-209, vol. 14.

Hirschel et al., "An Automated Hollow Fiber System for the Large Scale Manufacture of Mammalian Cell Secreted Product", Large Scale Cell Culture Technology, ed. Bjorn K. Lydersen, 1987, pp. 113-144, Hanser Publishers.

Nielsen, Lars Keld, "Bioreactors for Hematopoietic Cell Culture", Annu. Rev. Biomed. Eng., 1999, pp. 129-152, vol. 1.

Portner et al., An overview on Bioreactor Design, Prototyping and Process Control for Reproducible Three-Dimensional Tissue Culture, Drug Testing in Vitro: Breakthroughs and Trends in Cell Culture Technology, ed. Uwe Marx and Volker Sandig, 2007, pp. 53-78, Wiley-VCH.

Zhao et al., "Perfusion Bioreactor System for Human Mesenchymal Stem Cell Tissue Engineering: Dynamic Cell Seeding and Construct Development", Biotechnology and Bioengineering, Aug. 20, 2005, pp. 482-493, vol. 91, No. 4.

"International Search Report and Written Opinion", PCT/US2008/055915, Feb. 23, 2009.

Official Action, Japanese Patent Application No. 2009-552860, Apr. 24, 2012 (English language translation included).

Decision of Rejection, Japanese Patent Application No. 2009-552860, Dec. 17, 2012 (English language translation included).

Office Action, Canadian Patent Application No. 2,680,130, Feb. 5, 2014.

* cited by examiner

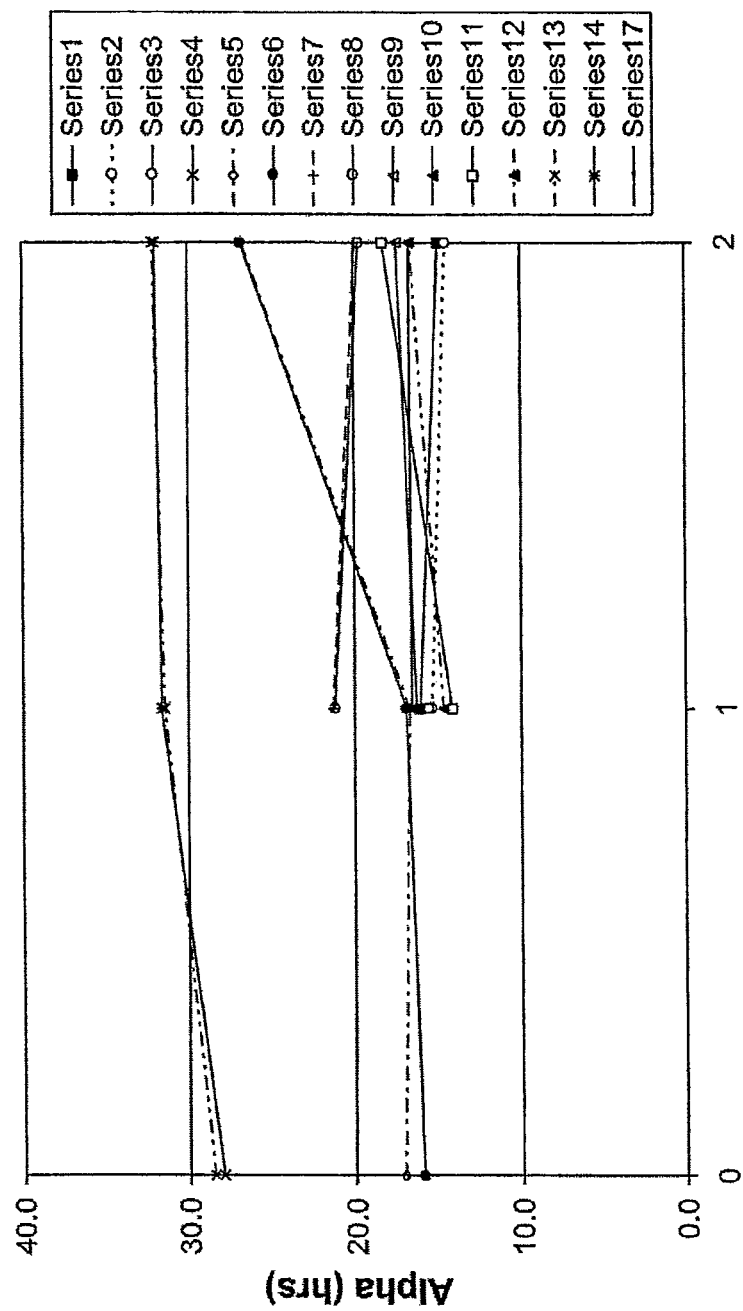

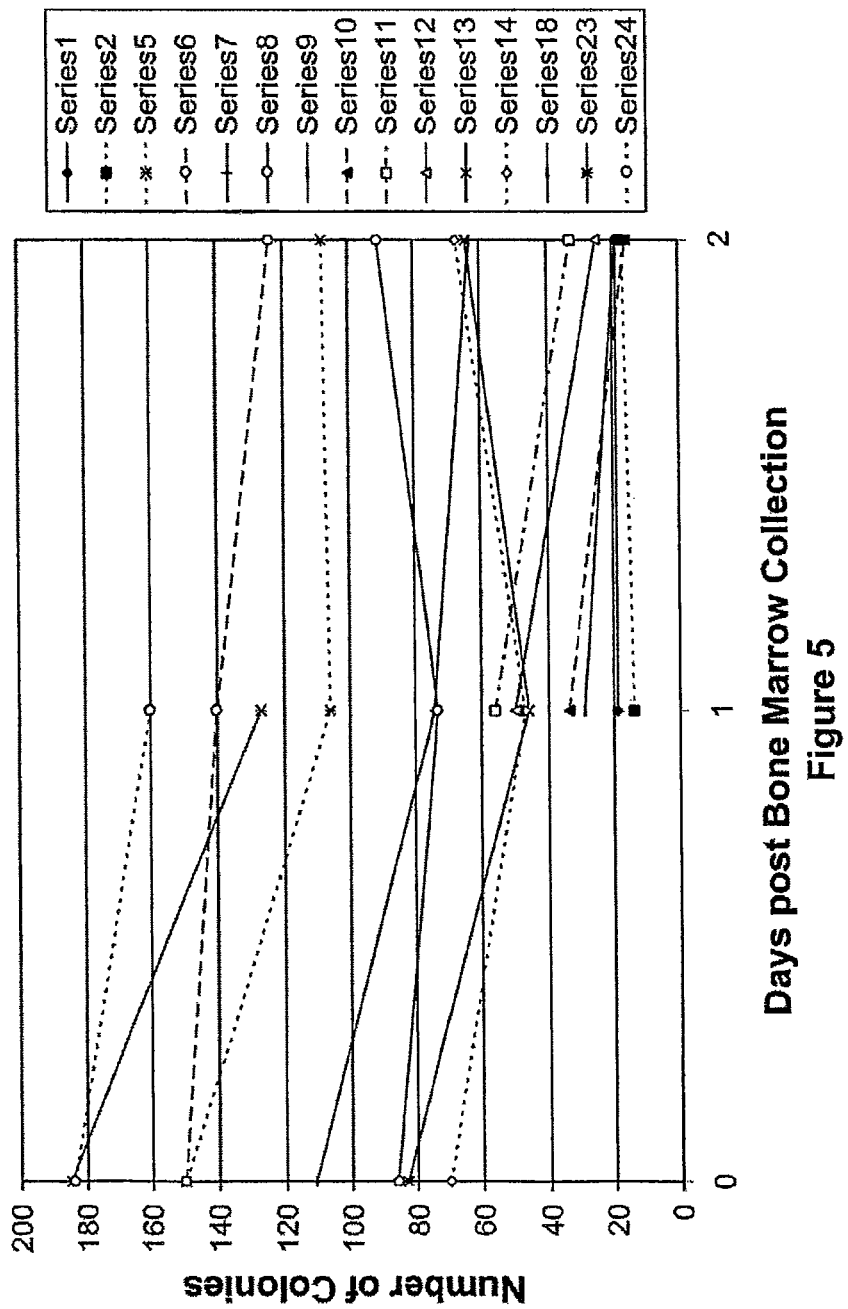

CELL EXPANSION SYSTEM AND METHODS OF USE

CROSS-REFERENCE TO RELATED APPLICATIONS

The present application is a divisional application of U.S. patent application Ser. No. 12/042,798, entitled, "CELL EXPANSION SYSTEM AND METHODS OF USE," filed Mar. 5, 2008 and issued as U.S. Pat. No. 8,309,347 on Nov. 13, 2012, which claims benefit under 35 U.S.C. §119(e) to U.S. Provisional Application Nos. 60/892,908, filed Mar. 5, 2007; 60/892,966, filed Mar. 5, 2007; 60/892,911, filed Mar. 5, 2007; 60/892,977, filed Mar. 5, 2007; 60/911,393, filed Apr. 12, 2007; 60/911,594, filed Apr. 13, 2007; and 60/971,494, filed Sep. 11, 2007. Each of these applications is incorporated herein by reference in its entirety.

FIELD

The present disclosure relates to cell expansion systems (CESs), associated cell growth chambers, and methods of using the same.

BACKGROUND

CESs are used to expand and differentiate cells. Cell expansion systems are known in the art. For example, U.S. Pat. No. 5,162,225 and U.S. Pat. No. 6,001,585 generally describe cell expansion systems designed for cell expansion.

The potential of stem cells in a variety of potential treatments and therapies have achieved particular attention. Stem cells which are expanded from donor cells can be used to repair or replace damaged or defective tissues and have broad clinical applications for a wide range of diseases. Recent advances in the regenerative medicine field demonstrates that stem cells have properties such as proliferation and self-renewal capacity, maintenance of the unspecialized state, and the ability to differentiate into specialized cells under particular conditions.

Cell expansion systems can be used to grow stem cells, as well as other types of cells. There is a need for cell expansion systems that can be used to grow adherent cells, non-adherent cells, and co-cultures of various cell types. The ability to provide sufficient nutrient supply to the cells, removing metabolites, as well as furnishing a physiochemical environment conducive to cell growth in a flexible system is an ongoing challenge. The present disclosure addresses these and other needs.

SUMMARY

In one aspect, the disclosure is directed to a CES including a first circulation path having a first fluid flow path with at least opposing ends. Opposing ends of the first fluid flow path are fluidly associated with opposing ends of a plurality of hollow fibers disposed in a cell growth chamber, such that fluid can flow through the first circulation path in a circuit. A first flow controller is operably linked to the first fluid flow path.

The cell expansion system further includes a second circulation path. The second circulation path includes a second fluid flow path with at least opposing ends. First and second ends of the second fluid flow path are fluidly associated with the cell growth chamber. A portion of the second fluid flow path is in fluid contact with the opposite side of one or more membranes in the cell growth chamber. A second fluid controller is operably linked to the second closed circuit path.

The cell expansion system further includes a first fluid supply line fluidly associated with the first circulation path and operably linked to a third fluid controller. The cell expansion system further includes a first fluid outlet path fluidly associated with the first or second circulation path. In various embodiments, the first fluid inlet path or the first fluid outlet path are operably associated with a third fluid flow controller.

In various embodiments, the CES is configured to allow fluid media in the first fluid circulation path to flow in a direction opposite to the direction of fluid media in the second fluid flow path ("counter-current"). Alternatively, the CES is configured to allow fluid media in the first fluid circulation path to flow in the same direction as fluid media in the second fluid flow path ("co-current").

In various additional aspects, the CES can be configured to add media to the first or second fluid circulation paths without exposing the CES to atmosphere.

In other aspects, the CES further includes an oxygenator. In certain variations, the oxygenator includes oxygenator inlet and outlet ports disposed in the oxygenator housing. Oxygenators can be part of the first circulation path or second circulation path. Oxygenators thus provide oxygen and/or other gases to the first or second fluid circulation paths.

In various other aspects, the present disclosure is directed to methods of expanding cells in the cell expansion system. Generally, cells are added to the first fluid flow path of the CES. Cells are then incubated under appropriate conditions to produce an expanded population of cells. This expanded population can then be harvested.

BRIEF DESCRIPTION OF THE DRAWINGS

The following figures illustrate non-limiting exemplary embodiments of the CESs disclosed herein, as well as components, uses thereof, and data relating thereto.

FIG. 4 depicts the effect of bone marrow age on number of MSC colonies.

FIG. 5 depicts the effect of bone marrow age on the MSC doubling time (alpha).

DETAILED DESCRIPTION

The present disclosure is generally directed to cell expansion systems and methods of using the same.

Figure 1A:
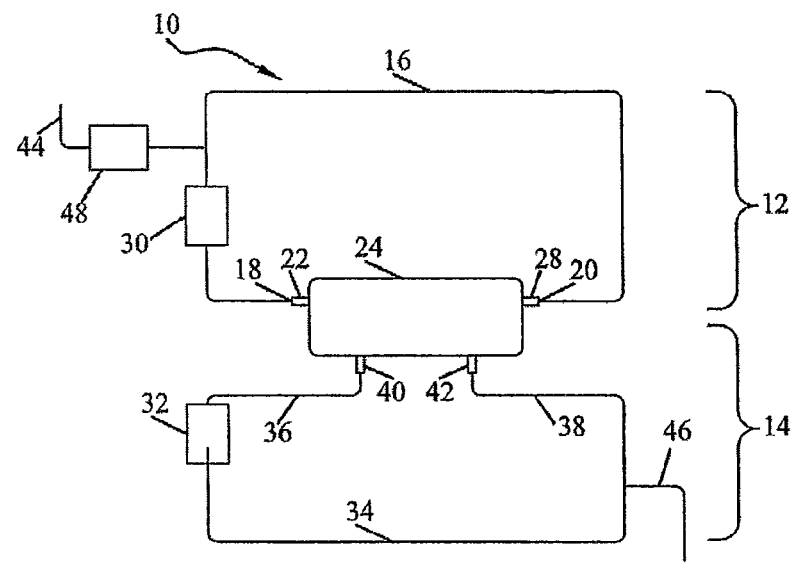
FIG. 1A depicts a flow diagram of one embodiment of a cell expansion system.

An exemplary schematic of a cell expansion system (CES) is depicted in FIG. 1A. CES 10 includes first fluid circulation path 12 and second fluid circulation path 14. First fluid flow path 16 has at least opposing ends 18 and 20 fluidly associated with a hollow fiber cell growth chamber 24 (also referred to herein as a "bioreactor"). Specifically, opposing end 18 is fluidly associated with a first inlet port 22 of cell growth chamber 24, and opposing end 20 is fluidly associated with first outlet port 28 of cell growth chamber 24. Fluid in first circulation path 12 flows through the interior of hollow fibers of hollow fiber membrane 50 disposed in cell growth chamber 24 (cell growth chambers and hollow fiber membranes are described in more detail infra). Further, first fluid flow controller 30 is operably connected to first fluid flow path 16, and controls the flow of fluid in first circulation path 12.

Second fluid circulation path 14 includes second fluid flow path 34, cell growth chamber 24, and a second fluid flow controller 32. The second fluid flow path 34 has at least opposing ends 36 and 38. Opposing ends 36 and 38 of second fluid flow path 34 are fluidly associated with a second inlet port 40 and a second outlet port 42 respectively of cell growth chamber 24. Fluid flowing through cell growth chamber 24 is in contact with the outside of hollow fiber membrane 50 in the cell growth chamber 24. Second fluid circulation path 14 is operably connected to second fluid flow controller 32.

First and second fluid circulation paths 12 and 14 are thus separated in cell growth chamber 24 by a hollow fiber membrane 50. Fluid in first fluid circulation path 12 flows through the intracapillary ("IC") space of the hollow fibers in the cell growth chamber. First circulation path 12 is thus referred to as the "IC loop." Fluid in second circulation path 14 flows through the extracapillary ("EC") space in the cell growth chamber. Second fluid circulation path 14 is thus referred to as the "EC loop." Fluid in first fluid circulation path 12 can flow in either a co-current or counter-current direction with respect to flow of fluid in second fluid circulation path 14.

Fluid inlet path 44 is fluidly associated with first fluid circulation path 12. Fluid inlet path 44 allows fluid into first fluid circulation path 12, while fluid outlet path 46 allows fluid to leave CES 10. Third fluid flow controller 48 is operably associated with fluid inlet path 44. Alternatively, a fourth fluid flow controller (not shown) can be associated with first fluid outlet path 46.

Fluid flow controllers as used herein can be a pump, valve, clamp, or combination thereof. Multiple pumps, valves, and clamps can be arranged in any combination. In various embodiments, the fluid flow controller is or includes a peristaltic pump. In further embodiments, fluid circulation paths, inlet ports, and outlet ports can be constructed of tubing of any material.

Various components are referred to herein as "operably associated." As used herein, "operably associated" refers to components that are linked together in operable fashion, and encompasses embodiments in which components are linked directly, as well as embodiments in which additional components are placed between the two linked components. "Operably associated" components can be "fluidly associated." "Fluidly associated" refers to components that are linked together such that fluid can be transported between them. "Fluidly associated" encompasses embodiments in which additional components are disposed between the two fluidly associated components, as well as components that are directly connected. Fluidly associated components can include components that do not contact fluid, but contact other components to manipulate the system (e.g. a peristaltic pump that pumps fluids through flexible tubing by compressing the exterior of the tube).

Generally, any kind of fluid, including buffers, protein containing fluid, and cell-containing fluid can flow through the various circulations paths, inlet paths, and outlet paths. As used herein, "fluid," "media," and "fluid media" are used interchangeably.

Cell Growth Chambers

The cell growth chamber of the cell expansion system generally includes a hollow fiber membrane comprised of a plurality of semi-permeable hollow fibers separating first and second fluid circulation paths.

Figure 2A:
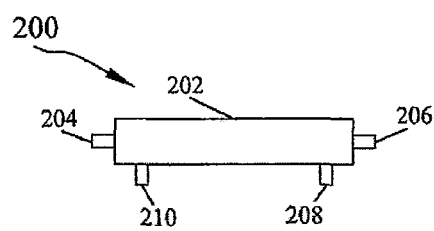
FIG. 2A depicts a side view of a hollow fiber cell growth chamber embodiment of a cell growth chamber.
Figure 2B:
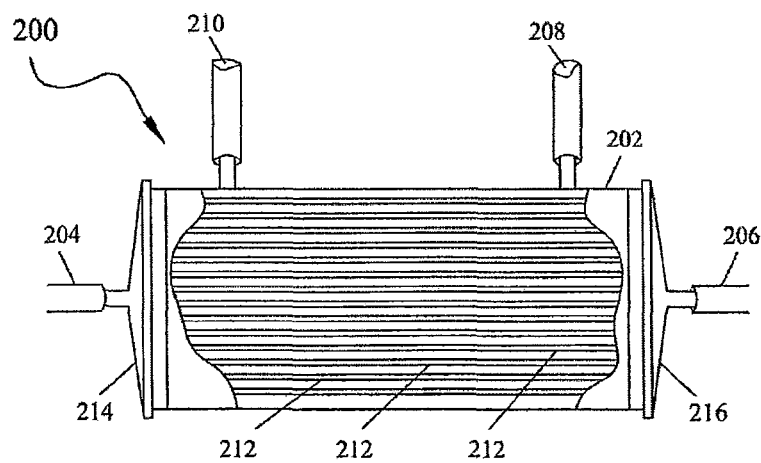
FIG. 2B depicts a cut-away side view of the hollow fiber cell growth chamber embodiment of FIG. 2A.

An exemplary cell growth chamber is depicted in FIG. 2, which depicts a cut-away side view of the hollow fiber cell growth chamber 200. Cell growth chamber 200 is bounded by cell growth chamber housing 202. Cell growth chamber housing 202 further includes four openings, or ports: inlet port 204, outlet port 206, inlet port 208, and outlet port 210.

Fluid in the first circulation path enters cell growth chamber 200 through inlet port 204, passes into and through the intracapillary side of a plurality of hollow fibers (referred to in various embodiments as the intracapillary ("IC") side or "IC space" of a hollow fiber membrane), and out of cell growth chamber 200 through outlet port 206. The terms "hollow fiber," "hollow fiber capillary," and "capillary" are used interchangeably. A plurality of hollow fibers are collectively referred to as a "membrane." Fluid in the second circulation path flows in the cell growth chamber through inlet port 208, comes in contact with the outside of the hollow fibers (referred to as the "EC side" or "EC space" of the membrane), and exits cell growth chamber 200 via outlet port 210. Cells can be contained within the first circulation path or second circulation path, and can be on either the IC side or EC side of the membrane.

Although cell growth chamber housing 202 is depicted as cylindrical in shape, it can have any other shape known in the art. Cell growth chamber housing 202 can be made of any type of biocompatible polymeric material. Various other cell growth chamber housings may differ in shape and size.

Those of skill in the art will recognize that the term cell growth chamber does not imply that all cells being grown or expanded in a CES are grown in the cell growth chamber. In many embodiments, adherent cells can adhere to membranes disposed in the growth chamber, or may grow within the associated tubing. Non-adherent cells (also referred to as "suspension cells") can also be grown. Cells can be grown in other areas within the first or second fluid circulation path.

For example, the ends of hollow fibers 212 can be potted to the sides of the cell growth chamber by a connective material (also referred to herein as "potting" or "potting material"). The potting can be any suitable material for binding the hollow fibers 212, provided that the flow of media and cells into the hollow fibers is not obstructed and that liquid flowing into the cell growth chamber through the IC inlet port flows only into the hollow fibers. Exemplary potting materials include, but are not limited to, polyurethane or other suitable binding or adhesive components. In various embodiments, the hollow fibers and potting may be cut through perpendicular to the central axis of the hollow fibers at each end to permit fluid flow into and out of the IC side. End caps 214 and 216 are disposed at the end of the cell growth chamber.

Fluid entering cell growth chamber 200 via inlet port 208 is in contact with the outside of hollow fibers. This portion of the hollow fiber cell growth chamber is referred to as the "extra-capillary (EC) space." Small molecules (e.g. water, oxygen, lactate, etc.) can diffuse through the hollow fibers from the interior of the hollow fiber to the EC space, or from the EC space to the IC space. Large molecular weight molecules such as growth factors are typically too large to pass through the hollow fibers, and remain in the IC space of the hollow fibers. The media may be replaced as needed. Media may also be circulated through an oxygenator to exchange gasses as needed.

In various embodiments, cells can be loaded into the hollow fibers by any of a variety of methods, including by syringe. The cells may also be introduced into the cell growth chamber from a fluid container, such as a bag, which may be fluidly associated with the cell growth chamber.

Hollow fibers are configured to allow cells to grow in the intracapillary space (i.e. inside the hollow fiber lumen) of the fibers. Hollow fibers are large enough to allow cell adhesion in the lumen without substantially impeding the flow of media through the hollow fiber lumen. In various embodiments, the inner diameter of the hollow fiber can be greater than or equal to 10000, 9000, 8000, 7000, 6000, 5000, 4000, 3000, 2000, 1000, 900, 800, 700, 650, 600, 550, 500, 450, 400, 350, 300, 250, 200, 150, or 100 microns. Likewise, the outer diameter of the hollow fiber can be less than or equal to 10000, 9000, 8000, 7000, 6000, 5000, 4000, 3000, 2000, 1000, 900, 800, 700, 650, 700, 650, 600, 550, 500, 450, 400, 350, 300, 250, 200, 150, or 100 microns. The hollow fiber wall thickness is sufficient to allow diffusion of small molecules.

Any number of hollow fibers can be used in a cell growth chamber, provided the hollow fibers can be fluidly associated with the inlet and outlet ports of the cell growth chamber. In various embodiments, the cell growth chamber can include a number of hollow fibers greater than or equal to 1000, 2000, 3000, 4000, 5000, 6000, 7000, 8000, 9000, 10000, 11000 or 12000. In other embodiments, the cell growth chamber can include a number of hollow fibers less than or equal to 12000, 11000, 10000, 9000, 8000, 7000, 6000, 5000, 4000, 3000, or 2000. In other various embodiments, the length of the hollow fibers can be greater than or equal to 100, 200, 300, 400, 500, 600, 700, 800, or 900 millimeters. In certain embodiments, the cell growth chamber contains approximately 9000 hollow fibers that have an average length of 295 mm, an average inner diameter of 215 microns, and an average outer diameter of 315 microns.

Hollow fibers can be constructed of any material capable of forming a size sufficient to form fibers capable of transporting liquid from the cell growth chamber inlet port to the cell growth chamber outlet port. In various embodiments, the hollow fibers can be constructed from plastic adherent materials capable of binding to certain types of cells, such as adherent stem cells (e.g. MSCs). In various other embodiments, hollow fibers can be treated with compounds such as fibronectin to form adherent surfaces.

In certain embodiments, the hollow fibers may be made of a semi-permeable, biocompatible polymeric material. One such polymeric material which can be used is a blend of polyamide, polyarylethersulfone and polyvinylpyrrolidone (referred to herein as "PA/PAES/PVP"). The semi-permeable membrane allows transfer of nutrients, waste and dissolved gases through the membrane between the EC space and IC space. In various embodiments, the molecular transfer characteristics of the hollow fiber membranes are chosen to minimize loss of expensive reagents necessary for cell growth such as growth factors, cytokines etc. from the hollow fiber, while allowing metabolic waste products to diffuse through the membrane into the hollow fiber lumen side to be removed.

In certain variations, one outer layer of each PA/PAES/PVP hollow fiber is characterized by a homogenous and open pore structure with a defined surface roughness. The openings of the pores are in the size range of 0.5-3 um, and the number of pores on the outer surface of the fibers are in the range of 10,000 to 150,000 pores per $mm^2$. This outer layer has a thickness of about 1 to 10 um. The next layer in each hollow fiber is a second layer having the form of a sponge structure and, in a further embodiment, a thickness of about 1 to 15 um. This second layer serves as a support for the outer layer. A third layer next to the second layer has the form of finger-like structures. This third layer provides mechanical stability and a high void volume which gives the membrane a very low resistance to transporting molecules through the membrane. During use, the finger-like voids are filled with fluid and the fluid gives a lower resistance for diffusion and convection than a matrix with a sponge-filled structure having a lower void volume. This third layer has a thickness of 20 to 60 um.

In further embodiments, the hollow fiber membrane can include 65-95% by weight of at least one hydrophobic polymer and 5-35% by weight of at least one hydrophilic polymer. The hydrophobic polymer may be chosen from the group consisting of polyamide (PA), polyaramide (PAA), polyarylethersulphone (PAES), polyethersulphone (PES), polysulphone (PSU), polyarylsulphone (PASU), polycarbonate (PC), polyether, polyurethane (PUR), polyetherimide and copolymer mixtures of any of the above polymers, such as polyethersulphone or a mix of polyarylethersulphone and polyamide. In additional embodiments, the hydrophilic polymer may be chosen from the group consisting of polyvinylpyrrolidone (PVP), polyethylene glycol (PEG), polyglycolmonoester, water soluble cellulosic derivates, polysorbate and polyethylene-polypropylene oxide copolymers.

Depending upon the type of cells to be expanded in the cell growth chamber, the polymeric fibers may be treated with a substance, such as fibronectin, to enhance cell growth and/or adherence of the cells to the membrane.

Cell Expansion Systems

Cell growth chambers such as the one depicted in FIG. 2 are operably associated with other components of cell expansion systems.

Figure 1E:
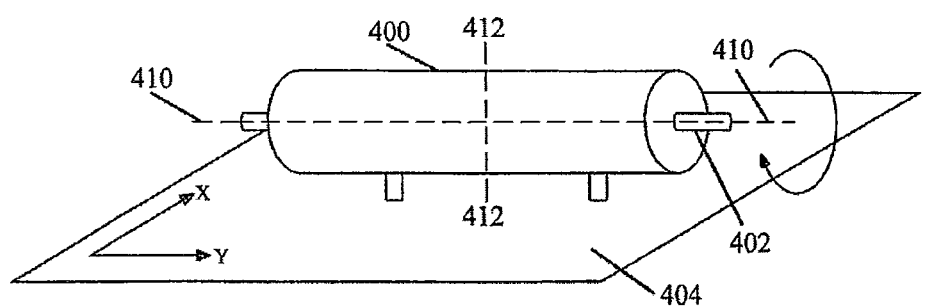
FIG. 1E depicts a rocking device for moving a cell growth chamber rotationally or laterally during operation of the CES.
Figure 1B:
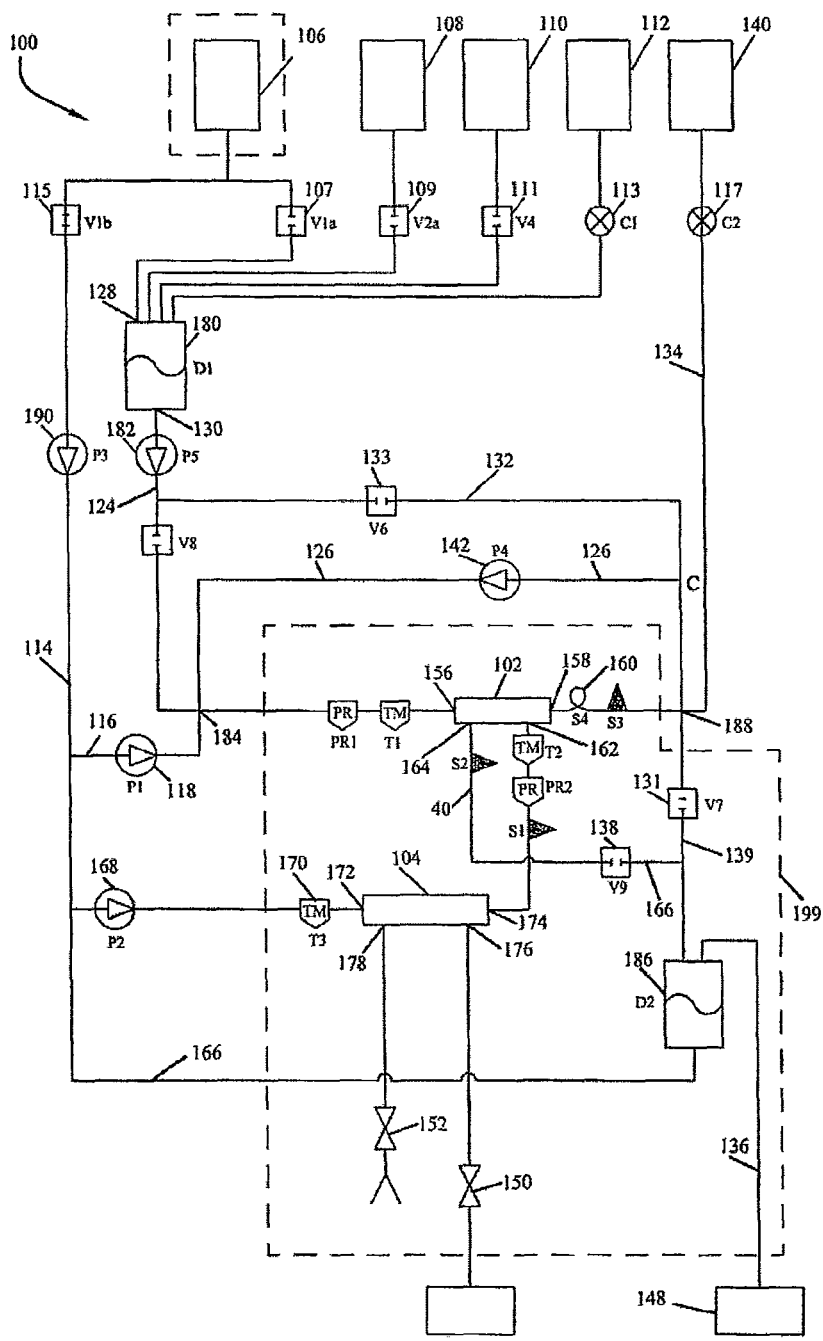
FIG. 1B depicts a flow diagram of one embodiment of a cell expansion system.

FIG. 1B depicts a more detailed cell expansion system 100. CES 100 includes first fluid circulation path 126 (also referred to as the "intracapillary (IC) loop") and second fluid circulation path 166. Fluid flow paths are constructed of tubing and tubing conduits (Tygothane, St. Globain) and operates in conjunction with valves, pumps and other components.

Outlet port 158 of cell growth chamber 102 is fluidly associated via tubing with inlet port 156, which together with cell growth chamber 102 form first fluid circulation path 126. In the embodiment depicted in FIG. 1B, first fluid circulation path 126 is configured for fluid to flow through cell growth chamber 102, sample coil 160, pump 142, and back through cell growth chamber 102. Cells can be flushed out of cell growth chamber 102 or redistributed along the hollow fiber membrane.

First fluid circulation path 126 also includes sample coil 160. Sample coil 160 allows samples of fluid in first fluid circulation path 126 to be obtained and tested.

CES 100 also includes second fluid circulation path 166 (also referred to as the "extracapillary loop" or "EC loop"). Second fluid circulation path 166 includes pump 168, temperature meter 170, and oxygenator 104. The second fluid flow path connects to oxygenator inlet port 172 and exits into oxygenator outlet port 174. Oxygenator outlet port 174 is associated with cell growth chamber 102 by inlet port 162, and departs cell growth chamber 102 via cell growth chamber outlet port 164. Second fluid circulation path 166 is configured for fluid to pass through valve 138, into drip chamber 186, and back through pump 168.

Second fluid circulation path 166 provides gas to the cells in cell growth chamber 102, and also allows for removal of waste metabolites produced by the cells. Gas flows into and out of oxygenator 104 via filters 150 and 152. Filters 150 and 152 prevent contamination of the oxygenator or associated media. Media flows into oxygenator inlet port 172, through fibers contained in oxygenator 104, and leaves through outlet port 174. Oxygen enters oxygenator 104 at gas inlet port 176. The concentration of gases in the oxygenator can be any concentration desired. Gases diffuse across the fibers in the oxygenator.

Fluid media contained in second fluid circulation path 166 is in equilibrium with the gases flowing in through gas inlet port 176. The amount of oxygen entering the media can be controlled by controlling the gas concentration. The mole percent (also referred to herein as "molar concentration") of oxygen in the gas phase before diffusing into the media is typically greater than or equal to 0%, 5%, 10% or 15%. Alternatively, the mole percent of oxygen in the gas is equal to or less than 20%, 15%, 10% or 5%. In certain embodiments, the molar concentration of oxygen is 5%. Various oxygenators known in the art can be used as well. Any commercial oxygenator can be used. In certain embodiments, oxygenators have a hollow fiber count of 1820, an internal fiber diameter of 280 μm, an outer fiber diameter of 386 μm and an intracapillary fluid volume of 16 mL.

CES 100 includes first fluid inlet path 124. First fluid inlet path 124 includes drip chamber 180 and pump 182. Fluid media and/or cells flow from EC media container 106 through valve 107; IC fluid media container 108 through valve 109; vent bag 110 through valve 111; or cell input bag 112 through clamp 113. Each of IC fluid media container 108, EC media container 106, vent bag 110, or cell input bag 112 are fluid media containers as discussed herein. IC media generally refers to media that circulates in first circulation path 126. EC media generally refers to media that circulates in second circulation path 166.

Drip chamber 180 helps prevent pockets of gas (e.g. air bubbles) from reaching cell growth chamber 102. Ultrasonic sensors can be disposed near entrance port 128 and exit port 130 of drip chamber 180. A sensor at entrance port 128 prevents fluids in drip chamber 180 from back-flowing into EC media container 106, IC media container 108, vent bag 110, cell input bag 112, or related tubing. A sensor at exit port 130 stops pump 182 if gas reaches the bottom of the sensor to prevent gas bubbles from reaching cell growth chamber 102.

CES 100 further includes second fluid inlet path 114. When valve 115 is opened, pump 190 can pump fluid from second fluid inlet path 114 into second fluid circulation path 166. Connector path 116 connects first circulation path and second circulation path. Pump 118 can pump fluid through connector path 116 from second fluid inlet path 114 into first fluid circulation path 126. Alternatively, fluid can be pumped between first fluid circulation path 126 and second fluid circulation path 166.

Those of skill in the art will recognize that fluid in first fluid circulation path 126 can flow through cell growth chamber 102 in either the same direction as fluid in second fluid circulation path 166 (co-current) or in the opposite direction of second fluid circulation path 166 (i.e. counter-current).

First fluid circulation path 126 is associated with first fluid inlet path 124 via flush line 132. Flush line includes valve 133, which can be opened and closed in combination with other valves and pumps to flow media to or from first fluid inlet path 124.

Likewise, first and second fluid flow paths are connected by fluid connector path 139. Valve 131 is disposed in fluid connector path 139. By opening valve 131 and using one or more pumps in CES 100, fluid can move between first fluid circulation path 126 and second fluid circulation path 166.

Cells can be harvested via cell harvest path 134. Cell harvest path 134 is fluidly associated with cell harvest bag 140 and first fluid circulation path 126 at junction 188. Cell harvest path 134 can be closed using clamp 117. Cells from cell growth chamber 102 can be pumped through cell harvest path 134 to cell harvest bag 140. Those of skill in the art will recognize that clamp 117 can be replaced by or combined with a valve, pump, or combination thereof in various embodiments.

Various components of the CES can be contained within incubator 199. Incubator 199 maintains cells and media at a constant temperature.

Fluid outlet path 136 is associated with drip chamber 186. Fluid outlet path 136 directs media from drip chamber 186 to waste bag 148.

As used herein, the terms "media bag," "vent bag" and "cell input bag" are arbitrary, in that their positions can be switched relative to other bags. For example, vent bag 110 can be exchanged with IC media container 108, or with cell bag 112. The input and output controls and parameters can then be adjusted to accommodate the changes. It will further be noted that the location of the drip chamber, or sensors independent of the drip chamber, can be at any location in the CES before inlet port 156.

Those of skill in the art will further recognize that the pumps and valves in the CES of FIG. 1B serve as fluid flow controllers. In various embodiments, fluid flow controllers can be pumps, valves, or combinations thereof in any order, provided that the first fluid circulation path and second fluid circulation path are configured to circulate fluid and fluid input path(s) are configured to add fluid.

The CES can include additional components. For example, one or more pump loops (not shown) can be added at the location of peristaltic pumps on the CES. Peristaltic pumps are operably connected to the exterior of tubing, and pumps liquid through the fluid flow path by constricting the exterior of the tubing to push liquid through the tubing. The pump loops may be made of polyurethane (PU) (available as Tygothane C-210A), neoprene based material (e.g. Armapure, St. Gobain), or any other suitable material. Alternatively, a cassette for organizing the tubing lines and which may also contain tubing loops for the peristaltic pumps may also be included as part of the disposable. One or more of the components of the CES can be contained in a cassette to aid in organizing the tubing.

In various embodiments, the CES can include sensors for detecting media properties such as pH, as well as cellular metabolites such as glucose, lactate, and oxygen. The sensors can be operably associated with the CES at any location in the IC or EC loops. Various commercially available pH, glucose, or lactate sensor can be used.

Figure 1C:
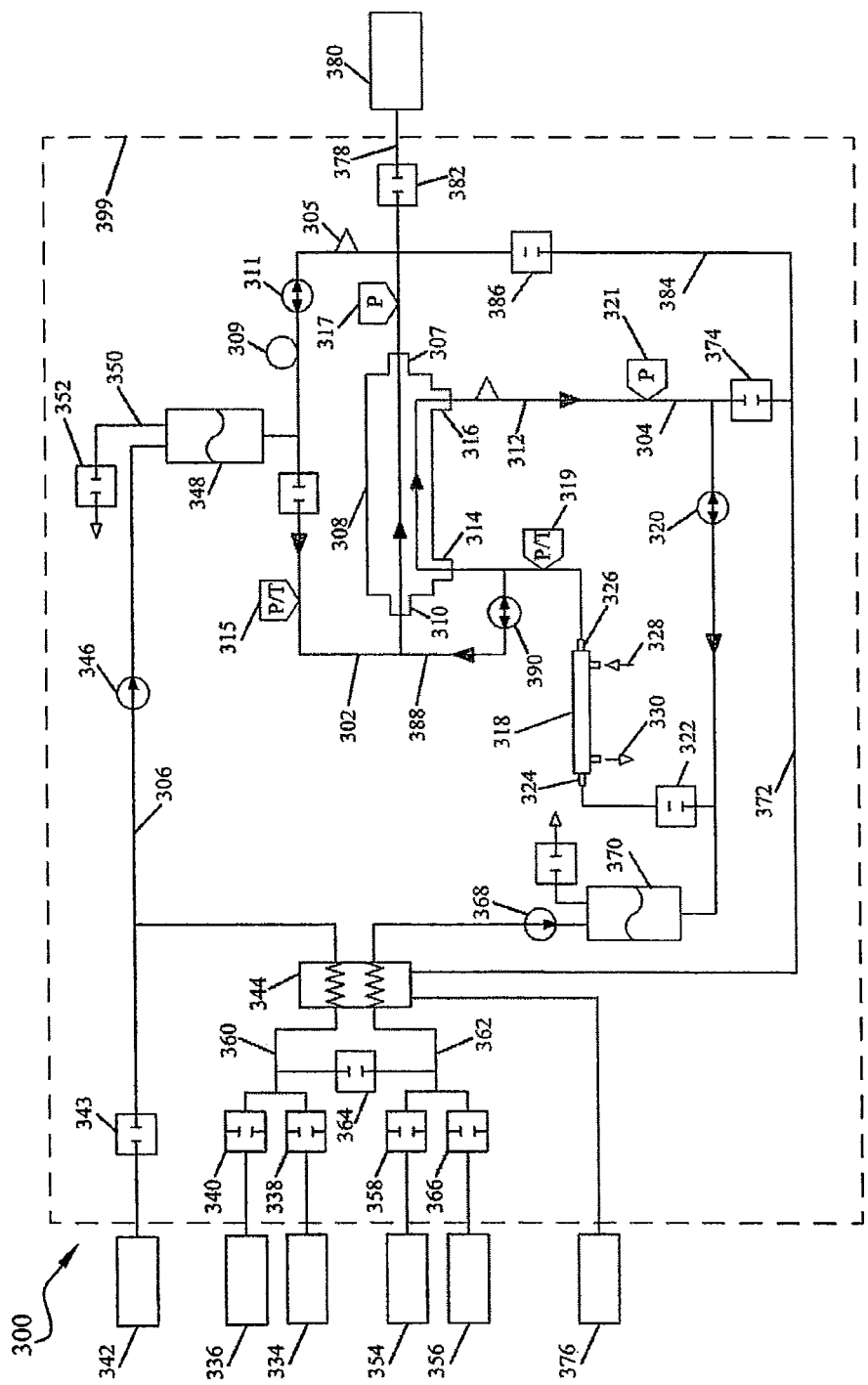
FIG. 1C depicts a flow diagram of another embodiment of a cell expansion system.

FIG. 1C depicts another embodiment of a CES. CES 300 includes first fluid circulation path 302 (also referred to as the "intracapillary (IC) loop") and second fluid circulation path 304 (also referred to as the "extracapillary loop" or "EC loop").

First fluid flow path 306 is fluidly associated with cell growth chamber 308 to form first fluid circulation path 302. Fluid flows into cell growth chamber 308 through inlet port 310, through hollow fibers in cell growth chamber 308, and exits via outlet port 307. Pressure gauge 317 measures the pressure of media leaving cell growth chamber 308. Media flows through valve 313 and pump 311, which can be used to control the rate of media flow. Samples of media can be obtained from sample port 305 or sample coil 309 during operation. Pressure/temperature gauge 315 disposed in first fluid circulation path allows detection of media pressure and temperature during operation. Media then returns to inlet port 310 to complete fluid circulation path 302. Cells expanded in cell growth chamber 308 can be flushed out of cell growth chamber 308 or redistributed within hollow fibers for further growth.

Second fluid circulation path 304 includes second fluid flow path 312 that is fluidly associated with cell growth chamber 308 in a loop. Fluid in second fluid circulation path 304 enters cell growth chamber 308 via inlet port 314, and leaves cell growth chamber 308 via outlet port 316. Media is in contact with the outside of the hollow fibers in the cell growth chamber 308, allowing diffusion of small molecules into and out of the hollow fibers.

Pressure/temperature gauge 319 disposed in the second circulation path allows the pressure and temperature of media to be measured before the media enters the EC space of the cell growth chamber 308. Pressure gauge 321 allows the pressure of media in the second circulation path to be measured after it leaves the cell growth chamber.

After leaving outlet port 316 of cell growth chamber 308, fluid in second fluid circulation path 304 passes through pump 320 and valve 322 to oxygenator 318. Second fluid flow path 312 is fluidly associated with oxygenator 318 via oxygenator inlet port 324 and oxygenator outlet port 326. In operation, fluid media flows into oxygenator 318 via oxygenator inlet port 324, and exits oxygenator 318 via oxygenator outlet port 326.

Oxygenator 318 adds oxygen to media in the CES. In various embodiments, media in second fluid circulation path 304 is in equilibrium with gas entering oxygenator. The oxygenator can be any oxygenator known in the art. Gas flows into oxygenator 318 via filter 328 and out of oxygenator 318 through filter 330. Filters 328 and 330 reduce or prevent contamination of oxygenator 318 and associated media.

In the configuration depicted for CES 300, fluid media in first circulation path 302 and second circulation path 304 flow through cell growth chamber 308 in the same direction (a co-current configuration). Those of skill in the art will recognize that CES 300 can also be configured in a counter-current conformation. Those of skill in the art will recognize that the respective inlet and outlet ports can be disposed in the cell growth chamber at any location.

Cells and fluid media can be introduced to fluid circulation path 302 via first fluid inlet path 332. Fluid container 334 and fluid container 336 are fluidly associated with first fluid inlet path 332 via valves 338 and 340 respectively. Likewise, cell container 342 is fluidly associated with first fluid circulation path 302 via valve 343. Cells and fluid proceed through heat exchanger 344, pump 346, and into drip chamber 348. Drip chamber 348 is fluidly associated with first circulation path 302. Overflow from drip chamber 348 can flow out of drip chamber 348 from overflow line 350 via valve 352.

Additional fluid can be added to first or second fluid circulation paths 302 and 304 from fluid container 354 and fluid container 356. Fluid container 354 is fluidly associated with valve 358 which is fluidly associated with first fluid circulation path 302 via first fluid inlet path 360. First fluid flow path includes valve 364. Alternatively, fluid container 354 is fluidly associated with second fluid inlet path 362. Likewise, fluid container 356 is fluidly associated with valve 366, which is fluidly associated with first fluid circulation path 302 via first fluid inlet path 360. Alternatively, fluid container 364 is fluidly associated with second fluid inlet path 362.

Second fluid inlet path 362 is configured to allow fluid to flow through pump 368 before entering drip chamber 370. Second fluid inlet path 362 continues to second fluid circulation path 304. Overflow fluid can flow out via overflow line 372 through valve 374 to waste container 376.

Cells can be harvested via cell harvest path 378. Cells from cell growth chamber 308 can be harvested by pumping media containing the cells through cell harvest path 378 to cell harvest bag 380.

First and second fluid circulation paths 302 and 304 are connected by connector path 384. When valve 386 is opened, media can flow through connector path 384 between first and second circulation paths 302 and 304. Likewise, pump 390 can pump media through another connector path 388 between first and second fluid circulation paths 302 and 304.

Various components of the CES can be contained within incubator 399. Incubator 399 maintains cells and media at a constant temperature.

As will be recognized by those of skill in the art, any number of fluid containers (e.g. media bags) can be fluidly associated with the CES in any combination. It will further be noted that the location of the drip chamber, or sensors independent of the drip chamber, can be at any location in the CES before inlet port 310.

The CES can include additional components. For example, one or more pump loops (not shown) can be added at the location of peristaltic pumps on the CES. The pump loops may be made of polyurethane (PU) (available as Tygothane C-210A)). Alternatively, a cassette for organizing the tubing lines and which may also contain tubing loops for the peristaltic pumps may also be included as part of the disposable.

Rocking Device

The CES can include a device configured to move or "rock" the cell growth chamber relative to other components of the cell expansion system by attaching it to a rotational and/or lateral rocking device. FIG. 1E shows one such device, in which a bioreactor 400 is rotationally connected to two rotational rocking components, and a lateral rocking component.

A first rotational rocking component 402 rotates the bioreactor around central axis 410 of the bioreactor. Rotational rocking component 402 is rotationally associated to bioreactor 400. Bioreactor 400 can be rotated continuously in a single direction around central axis 410 in a clockwise or counterclockwise direction. Alternatively, bioreactor 400 can rotate in alternating fashion, first clockwise, then counterclockwise around central axis 410.

The CES can also include a second rotational rocking component that rotates bioreactor 400 around rotational axis 412. Rotational axis 412 passes through the center of point of bioreactor 400 and is normal to central axis 410. Bioreactor 400 can be rotated continuously in a single direction around rotational axis 412 in a clockwise or counterclockwise direction. Alternatively, bioreactor 400 can be rotated around rotational axis 412 in an alternating fashion, first clockwise, then counterclockwise. In various embodiments, bioreactor 400 can also be rotated around rotational axis 412 and positioned in a horizontal or vertical orientation relative to gravity.

Lateral rocking component 404 is laterally associated with bioreactor 400. The plane of lateral rocking component 404 moves laterally in the –x and –y directions.

The rotational and/or lateral movement of the rocking device can reduce the settling of cells within the device and reduce the likelihood of cells becoming trapped within a portion of the bioreactor. The rate of cells settling in the cell growth chamber is proportional to the density difference between the cells and the suspension media according to Stoke's Law. In certain embodiments, a 180 degree rotation (fast) with a pause (having a total combined time of 30 seconds) repeated as described above keeps non-adherent red blood cells suspended (data not shown). A minimum rotation of about 180 degrees would be preferred; however, one could use rotation of up to 360 degrees or greater. Different rocking components can be used separately, or can be combined in any combination. For example, a rocking component that rotates bioreactor 400 around central axis 410 can be combined with the rocking component that rotates bioreactor 400 around axis 412. Likewise, clockwise and counterclockwise rotation around different axes can be performed independently in any combination.

Detachable Flow Circuit

A detachable flow circuit (also referred to herein as a "detachable circulation module") is also provided. The detachable flow circuit is a portion of a cell expansion module configured to attach to a fixed portion of the CES. Generally, the fixed portions of the CES include peristaltic pumps. In various embodiments, the fixed portions of the CES can include valves and/or clamps.

The detachable flow circuit can include a first fluid flow path having at least opposing ends. The first end is configured to be fluidly associated with a first end of a cell growth chamber, and a second end of the first fluid flow path configured to fluidly associated with an opposing end of the cell growth chamber.

Likewise, the detachable flow circuit can include a second fluid flow path having at least two opposing ends. Portions of the detachable flow circuit can be configured to be fluidly associated with an oxygenator and/or bioreactor. The detachable flow circuit can include a second fluid flow path that is configured to fluidly associate with the oxygenator and cell growth chamber.

In various embodiments, the detachable flow circuit is detachably and disposably mounted to a fluid flow controller. The detachable flow circuit can include detachable fluid conduits (e.g. flexible tubing) that connect portions of the CES. With reference to FIG. 1F, the detachable flow circuit includes the tubing for first fluid circulation path 126, but without pump 142. The detachable flow circuit can further include the tubing for flush line 132, without valve 133. The detachable flow circuit can further include the tubing connecting first circulation path 126 to flush line 132, and first fluid inlet path 124. In various other permutations, the detachable flow circuit can include tubing that connects the media inlet bags 106 and 108, vent bag 110, and cell input bag 112 to drip chamber 180. The detachable flow circuit can also include tubing connecting cell harvest bag 140 to first circulation path 126.

Likewise, the detachable flow circuit can include tubing that makes up second circulation path 166. For example, the tubing can include tubing connecting oxygenator 104 to cell growth chamber 102, as well as drip chamber 186. The detachable flow circuit can also include fluid inlet path 114.

In further embodiments, the detachable flow circuit can include a cell growth chamber, oxygenator, as well as bags for containing media and cells. In various embodiments, the components can be connected together, or separate. Alternatively, detachable flow circuit can include one or more portions configured to attach to fluid flow controllers, such as valves, pumps, and combinations thereof. In variations where peristaltic pumps are used, the detachable circuit module can include a peristaltic loop configured to fit around a peristaltic portion of the tubing. In various embodiments, the peristaltic loop can be configured to be fluidly associated with the circulations paths, inlet paths, and outlet paths.

The detachable flow circuit can be combined in a kit with instructions for its assembly or attachments to fluid flow controllers, such as pumps and valves.

Priming the CES

Prior to adding cells, a CES can be "primed" with the media to prepare the CES for operation.

Priming the CES is described in further reference to CES 100 of FIG. 1B. First fluid circulation path 126 is primed before cell growth chamber 102 is attached to CES 100. Media is allowed to flow from EC media container 106 past valve 107, into drip chamber 180 and through first fluid inlet path 124 to junction 184. Drip chamber 180 is then filled with media.

First fluid circulation path 126 is then primed with EC media. Media is pumped from drip chamber 180 through flush line 132. Media also flows through first fluid circulation path 126 to junction 184.

Cell growth chamber 102 is then sterile docked into the system by orienting inlet port 156 in a downward direction and outlet port 158 in an upward facing direction. Media is pumped through second fluid inlet path 114 and first fluid inlet path 124. Air is pumped from cell growth chamber 102 to vent bag 110. Specific protocols are described below.

Second fluid circulation path 166 is then primed. Media in second fluid circulation path 166 flows through oxygenator 104, inlet port 162, outlet port 164, and through oxygenator 104 to complete second circulation path 166. Specific protocols are described below.

Variations on priming the CES can be used. For example, the CES can be primed with the cell expansion system attached to CES 100. Media from EC media container 106 or IC media container 108 can be used. Generally, media is added to the system to prevent gas pockets from forming in the system.

Media Exchange

Media circulating in either the IC or EC loop can be exchanged with fresh media without removing cells from the CES. IC media can be replaced with fresh IC media, and EC media can be replaced with fresh EC media.

In one embodiment, media can be exchanged by removing used media through the hollow fiber membranes in the cell growth chamber (referred to herein as "ultrafiltration"). In various embodiments, ultrafiltration is accomplished using a cell growth chamber having hollow fibers constructed from PA/PAES/PVP. With reference to FIG. 1B, fresh media is supplied to drip chamber 180, where it is then allowed to flow to junction 184. At least a portion of used media leaves first circulation path 126 by diffusing through the hollow fibers of cell growth chamber 102 to enter second circulation path 166 (the "EC loop"). Used media enters drip chamber 186, where it is flushed from the system via fluid outlet path 136 to waste bag 148. Ultrafiltration can be used for both adherent and non-adherent cells. Generally, large molecules such as proteins are too large to pass through the hollow fiber membranes. Ultrafiltration methods can limit the ability to remove large molecules from the system.

Alternatively, used media can be removed via connector flow path 139. Fresh media is supplied to drip chamber 180. Valve 131 is opened, and used media leaves first circulation path 126 via connector flow path 139. The used media is collected in drip chamber 186. Used media is then flushed from the system via fluid outlet path 136 to waste bag 148. EC media can be taken to waste bag 148 through drip chamber 186.

Used EC media can also be exchanged with fresh EC media. With reference to FIG. 1B, fluid is directed from EC media container 106, through valve 115, and directed to the EC loop via pump 190 and pump 168.

Entire volumes of media in the IC loop and EC loop can be readily exchanged without removing cells from the CES. Small volumes of media or other solution phase compounds can be added to the system as well. The multiple methods of media exchange further allow media to be exchanged without removing cells adhered to the cell growth chamber hollow fibers.

Introducing Cells to the CES

Cells can be added to the CES by a number of methods.

In a first exemplary method, cells can be added to CES 100 by ultrafiltration (also referred to as "high flux"), in a similar fashion to media exchange ultrafiltration described above. Cells from cell input bag 112 are passed through drip chamber 180 with EC and/or IC media at a high flow rate to push the cell-containing media into cell growth chamber 102. Subsequently, an excess volume of EC and/or IC media ("chase media") is loaded into drip chamber 180 and flowed through cell growth chamber 102. The chase media can be any media compatible with cells (for example IC media, EC media, or phosphate buffer solution (PBS)). The cells are distributed in hollow fibers of cell growth chamber 102.

Adherent cells (e.g. mesenchymal stem cells, or MSCs) can be selected based on adhesion to the hollow fiber lumen. The hollow fiber lumen can be constructed of an adherent material. Alternatively, the hollow fiber can be treated with fibronectin to cause cell adhesion.

In a second exemplary method, cells can be introduced to the CES by "passively loading" cells onto the media. Cells are introduced from drip chamber 180 into cell growth chamber 102. Media flow is stopped at junction 188. The volume of the cells and chase media is monitored to ensure that cells do not leave first fluid circulation path 126.

Cell Expansion

Cells can be grown ("expanded") in either the IC loop or the EC loop. Adherent and non-adherent suspension cells can be expanded.

In one embodiment, the lumen of the cell growth chamber fibers can be coated with fibronectin. Divalent cation-free (e.g. calcium and magnesium-free) PBS is added to the system. After adherent cells are introduced into cell growth chamber 102, they are incubated for a sufficient time to adhere to the hollow fibers. IC and EC media are circulated to ensure sufficient nutrients are supplied to the cells.

The flow rate of the IC loop and EC loop can be adjusted to a specific value. In various embodiments, the flow rate of the IC loop and EC loops can be, independently, equal to and/or less than 2, 4, 6, 8, 10, 15, 20, 25, 30, 35, 40, 45, 50, 60, 70, 80, 90, 100, 200, 300, 400, or 500 mL/minute. In various embodiments of the CES of FIG. 1B, the flow rate for the IC loop is 10-20 mL/minute, and the flow rate of the EC loop is 20-30 mL per minute (allowing media to flow through oxygenator 104 and re-establish oxygen levels). Pump 190 can optionally pump additional media into the CES at a low flow rate (e.g. 01. mL per minute) to replace media that evaporates through the tubes and oxygenator 104. In various embodiments, the EC loop removes cellular waste, and the IC loop includes growth factors in the media.

The CES provides a great deal of flexibility in varying growth conditions and criteria. Cells can be kept in suspension in the IC loop by circulating media continuously. Alternatively, media circulation can be stopped, causing cells to settle. Fresh media can be added to the IC loop by ultrafiltration to accommodate excess volume without removing cells. EC media circulation allows for exchange of gas, nutrients, waste products, and addition of new media without removing cells.

Expanded cells can include adherent cells, non-adherent cells, or a co-culture of any combination of cells in the art.

Cell Harvest

To harvest adherent cells, the IC and EC media are replaced with media that is free of divalent cations (e.g. divalent cation-free PBS). Trypsin is then loaded into first circulation path 126, and allowed to incubate with adherent cells for a period of time (e.g. 9-10 minutes). The trypsin is then flushed from the system. A shearing force is applied to the cells by increasing the flow rate through cell growth chamber, and adherent cells that are released from the cell growth chamber are pumped via cell harvest path 134 to cell harvest bag 140.

When non-adherent cells are expanded, the cells can be flushed from the circulating IC loop. Adherent cells remain in cell growth chamber 102, while non-adherent cells are removed.

The CES can be used to perform a variety of cell expansion methods.

In one embodiment, a seeded population of cells can be expanded. Cells are introduced, or seeded, into the CES. In certain circumstances, the lumen of the hollow fibers can be conditioned to allow cell adhesion. Cells are then added to the cell growth chamber, and adherent cells adhere to the hollow fibers, while non-adherent cells (e.g. hematopoetic stem cells, or HSCs) do not adhere. The non-adherent cells can be flushed from the system. After incubation for a period of time, the adherent cells can be released and harvested.

Stem cells, progenitor cells, and fully differentiated cells can all be expanded.

EXAMPLES

The following non-limiting examples illustrate various aspects of CES operation.

Example 1

50 mL bone marrow was loaded into a hollow fiber growth chamber of the CES depicted in FIG. 1B.

The cell input bag 108 was prepared with 50 mL bone marrow diluted 1:1 with IC media and connected drip chamber 180. 300 mL of EC Media was separately prepared.

Second circulation path 166 (i.e. EC loop) was conditioned by circulating EC media in second circulation path 166 while adding a small amount of EC media to replace fluid that evaporates from the system. Gas concentration, pH, and temperature of the circulating system were measured to insure proper function.

A solution containing bone marrow was then added to the system. A rocker operably attached to cell growth chamber 102 was turned on to minimize cell loss. Residual bone marrow was washed into the harvest bag to prevent the hollow fibers from clogging and help to rinse residual cells from the drip chamber.

Bone marrow cells were then circulated through the IC loop at 20 mL per minute, and EC media was circulated through the EC loop. A small amount of media was added regularly to both the IC loop and EC loop to prevent formation of gas bubbles in the system and tube collapse due to outgassing.

The media was replaced periodically by media exchange. EC media was prepared and placed in the EC media container 106. Drip chamber 180 was drained and refilled with EC media. EC media was then added to first fluid circulation path 126 (i.e. the IC loop). Cells were flushed to harvest bag 140 until the EC media was completely removed from drip chamber 180.

IC media was then added to CES 100 by flushing drip chamber 180 three times with IC media.

Example 2

MSCs were loaded into the CES.

CES 100 was prepared as described in Example 1. Media was added to both first and second circulation paths 126 and 166 of CES 100. Cell input bag 112 containing the MSCs suspended in 50 mL of IC media was prepared and attached to drip chamber 180. EC media container 106 was connected to drip chamber 180 and to second fluid inlet path 114. The cells were loaded into drip chamber 180. Pump 182 was set to a high flow rate, and cells were allowed to flow into cell growth chamber 102. 50 mL chase media of protein-containing IC media was then loaded into drip chamber 182 and loaded onto cell growth chamber 102.

EC media was circulated through the second circulation path 166 (the EC loop) at a flow rate of 20 mL/minute. Media in first circulation flow path 126 (the IC loop) was circulated at a flow rate of 10 mL per minute, and the cell population was allowed to expand.

Example 3

Adherent cells were collected from the CES.

The IC and EC media were replaced with divalent cation-free PBS as described in the media exchange section above. Trypsin was added to cell growth chamber 102 and allowed to incubate with adherent cells for 9-10 minutes. The trypsin was flushed very quickly from the system, and a shearing force was applied to the hollow fibers in cell growth chamber 126 by increasing the flow rate. The adherent cells released from the hollow fibers were flushed from cell growth chamber 126 by stopping the first circulation path and pumping the cell-containing media to harvest bag 140.

To harvest non-adherent cells, no trypsin was added, and cells were flushed from the first circulation path 126 to cell harvest bag 140. Adherent cells remained adhered to hollow fibers in the cell growth chamber, while non-adherent cells were collected.

Example 4

Non-adherent cells are loaded into the CES.

With reference to FIG. 1B, the cells are loaded in media from cell input bag 112 into drip chamber 180. The cells are then pumped slowly by pump 182 into cell growth chamber 102. The flow rate is adjusted to allow the cells to settle in the hollow fibers of the cell growth chamber 102. The flow rate is stepped down to steadily decreasing pressures as cells are loaded until all cells are pumped from drip chamber 180 into cell growth chamber 102.

Alternatively, non-adherent cells are loaded into the CES by ultrafiltration. The cells moved from cell input bag 112 into drip chamber 180. Pump 182 pumps cells into and through cell growth chamber 102 into first circulation path 126.

Subsequently, the cells are concentrated in the cell growth chamber by media exchange. IC media is added to first circulation path 126 from drip chamber 180. Pump 182 pumps media into cell growth chamber 102 through inlet port 156. Simultaneously, pump 142 pumps media into cell growth chamber 102 through outlet port 158. Excess media diffuses through the hollow fibers into second circulation path 166. Non-adherent cells are thus concentrated in the hollow fibers of cell growth chamber 102 by flowing media into the cell growth chamber 102 from both directions.

Flow rates can be tested using synthetic beads capable of entering the hollow fibers of the cell growth chamber. The beads can have different sizes and densities corresponding to different cell types. The circulation rate was reduced slowly, and the distribution of beads in cell growth chamber 102 was measured to determine if the flow rate changed bead distribution.

In various embodiments, adherent and non-adherent cells can be grown simultaneously. In one alternative, adherent cells are loaded and allowed to adhere to cell growth chamber 102. Suspension cells are then added to first circulation path 126. In a second alternative, suspension cells are loaded into cell growth chamber 102 first, and allowed to coat the surface of the hollow fibers in cell growth chamber 126, thereby promoting adherent cell growth and/or attachment. In a third alternative, the suspension cells are added to the CES first, and allowed to grow for a specific period of time. Suspension cells are then removed, and adherent cells are added to the system and allowed to adhere to the hollow fibers of the CES. Fresh suspension cells are then added, and grown simultaneously with the adherent cells.

In other alternatives, suspension cells and adherent cells are grown on different sides of the cell growth chamber. For example, adherent cells can be grown on the IC side, and suspension cells on the EC side, or vice versa. Adherent and suspension cells (e.g. MSCs and HSCs) can thus be maintained separately, but kept in fluid communication with each other across the membrane. Adherent cells and suspension cells can also be grown together on both the IC and EC sides of the cell growth chamber.

Example 5

Non-adherent cells were expanded in a CES.

Figure 1D:
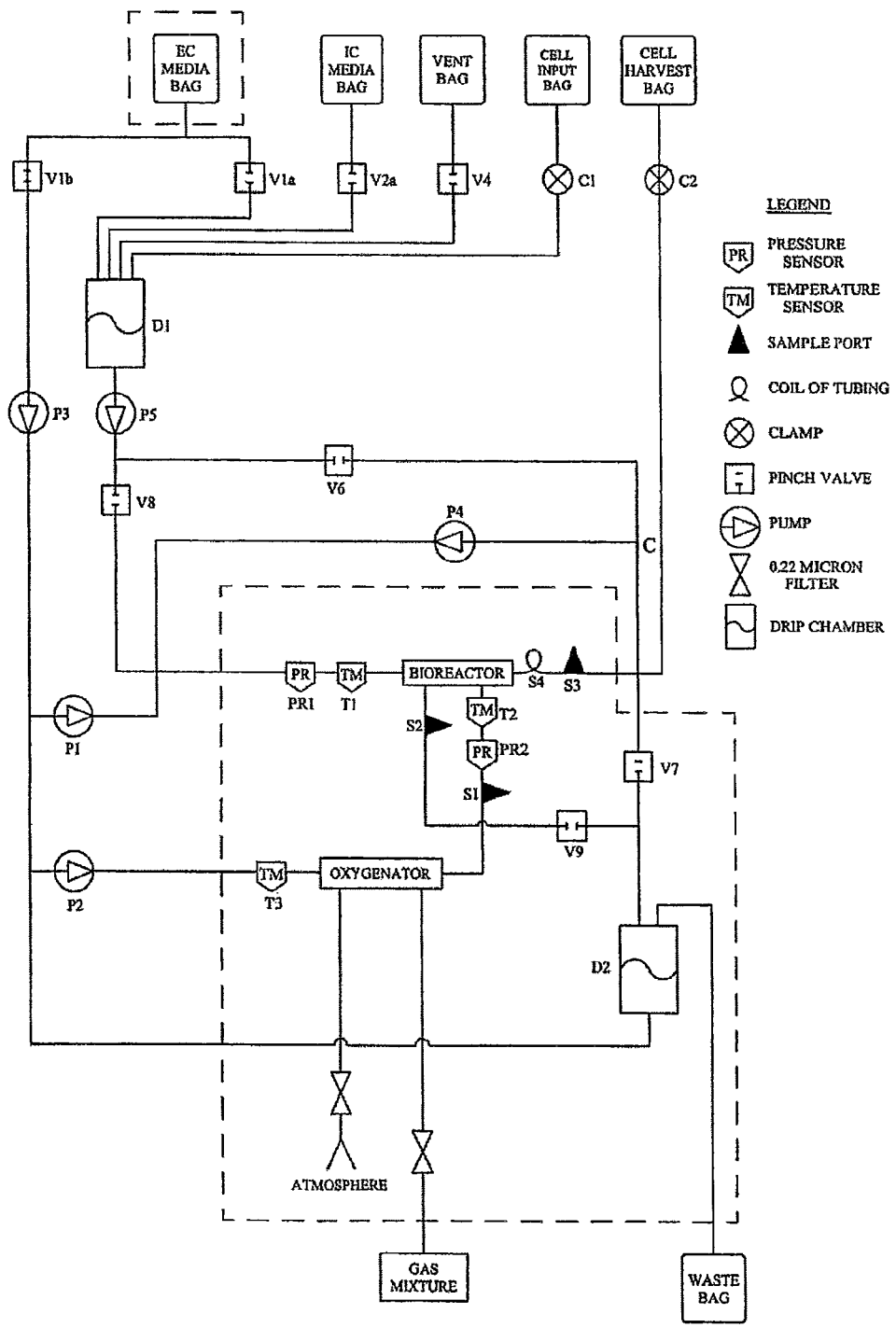
FIG. 1D depicts an embodiment of a CES similar to that of FIG. 1B.
Figure 1F:
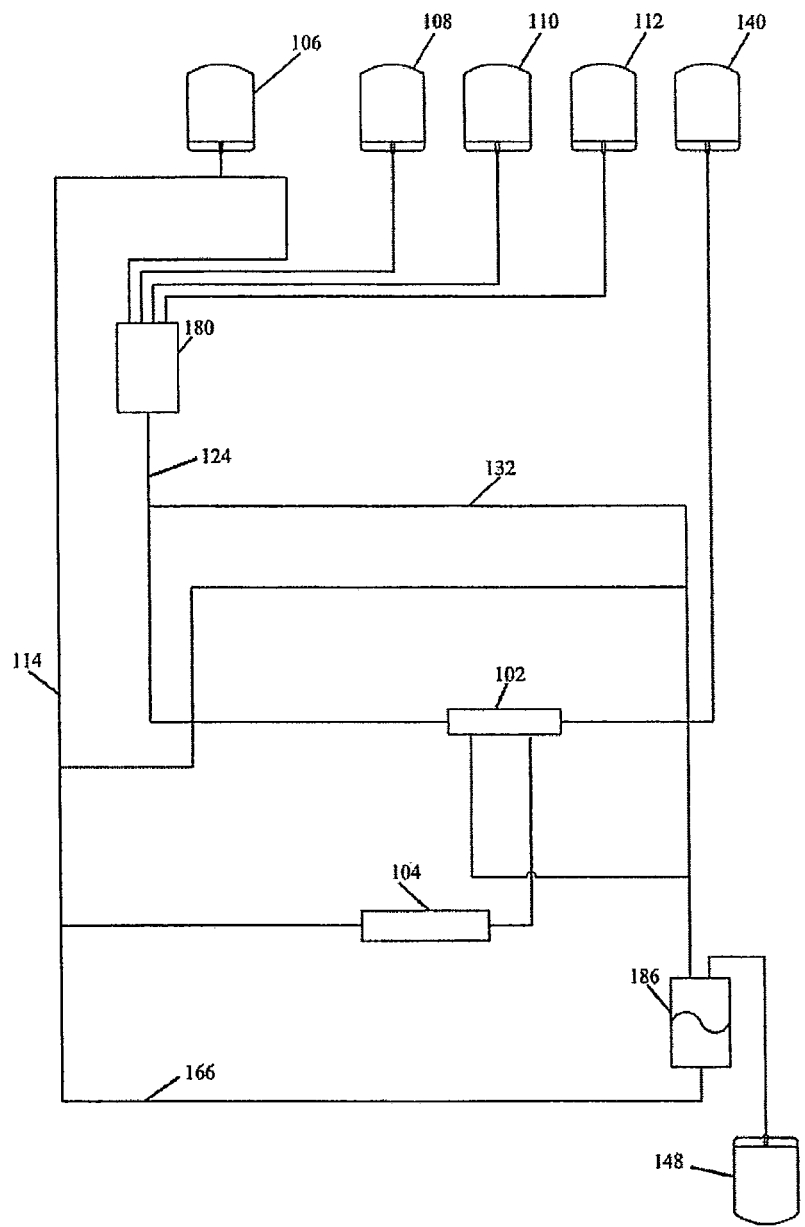
FIG. 1F depicts an embodiment of a detachable flow circuit.

A series of protocols were developed for various functions of a hollow fiber CES embodiment depicted in FIG. 1D (the CES embodiment depicted in FIG. 1D is substantially similar to the CES embodiment depicted in FIG. 1B). FIG. 1D discloses an embodiment having specific pumps (P1-P5), valves (V1a, V1b, V2a, V4, V6, V7, V8 and V9), clamps (C1 and C2), sample ports (S1-S3), drip chambers (D1 and D2), temperature gauges T1-T3, and pressure gauges PR1 and PR2. Various protocols were developed for priming, draining and filling drip chambers, exchanging fluid media between first and second fluid circulations paths, loading, expanding, harvesting cells, and removing air from the system.

FIGS. 6A-17 depict flow diagrams that show exemplary processes of using the CES. Each block diagram depicts pressure in units of mL per minute, opening and closing of valves, pressure gauges, and connecting of various components.

FIGS. 6A, 6B, 6C, and 6D depict a flow diagram protocol for priming the CES of FIG. 1D. The CES was first primed with EC media. EC media was pumped from the EC media bags into the EC loop by pumps P3 and P1. Drip chamber D1 was filled with EC media. Pumps P4 and P5 pumped EC media through the IC loop, and excess EC media flowed into drip chamber D2. The bioreactor was attached to the system, oriented vertically with respect to gravity, and pumps P3 and P5 filled the IC loop (including the bioreactor) and the EC loop with EC media. The waste bag was hung above the CES, and pumps P2 and P3 pumped media into the EC loop. Pumps P1, P2, P3 and P5 (at a high flow rate) then pumped media through the system, and excess media was allowed to flow through valve V7 to drip chamber D2.

Figure 7:
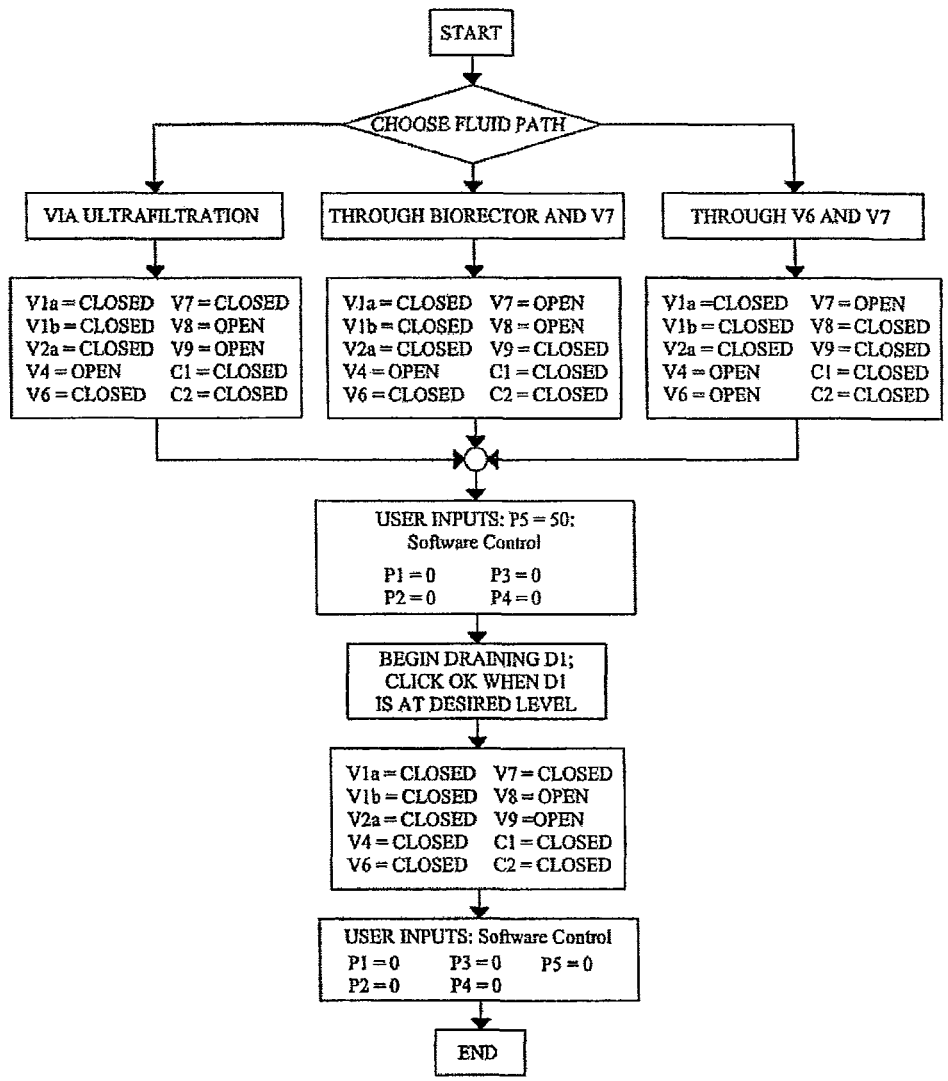
FIG. 7 depicts a flow chart protocol for draining the CES of FIG. 1D.

FIG. 7 depicts a flow diagram protocol for adding media from drip chamber D1 into the CES of FIG. 1D. Drip chamber D1 was filled with media chosen from any source, including IC media, EC media, and cells. One of three individual protocols can then be performed. In the first protocol, new media from drip chamber D1 was pumped through valve V6 in the IC loop, with excess media leaving the IC loop via valve V7. In the second protocol, media was pumped through the bioreactor, and exited the system via valve V7 and into drip chamber D2. In the third protocol, new media replaced used media via ultrafiltration, by pumping media at a high flow rate through the hollow fiber membrane in the bioreactor, and draining media from the system through valve V8 and into drip chamber D2. Media in drip chamber D2 then was allowed to flow to the waste bag.

Figure 8:
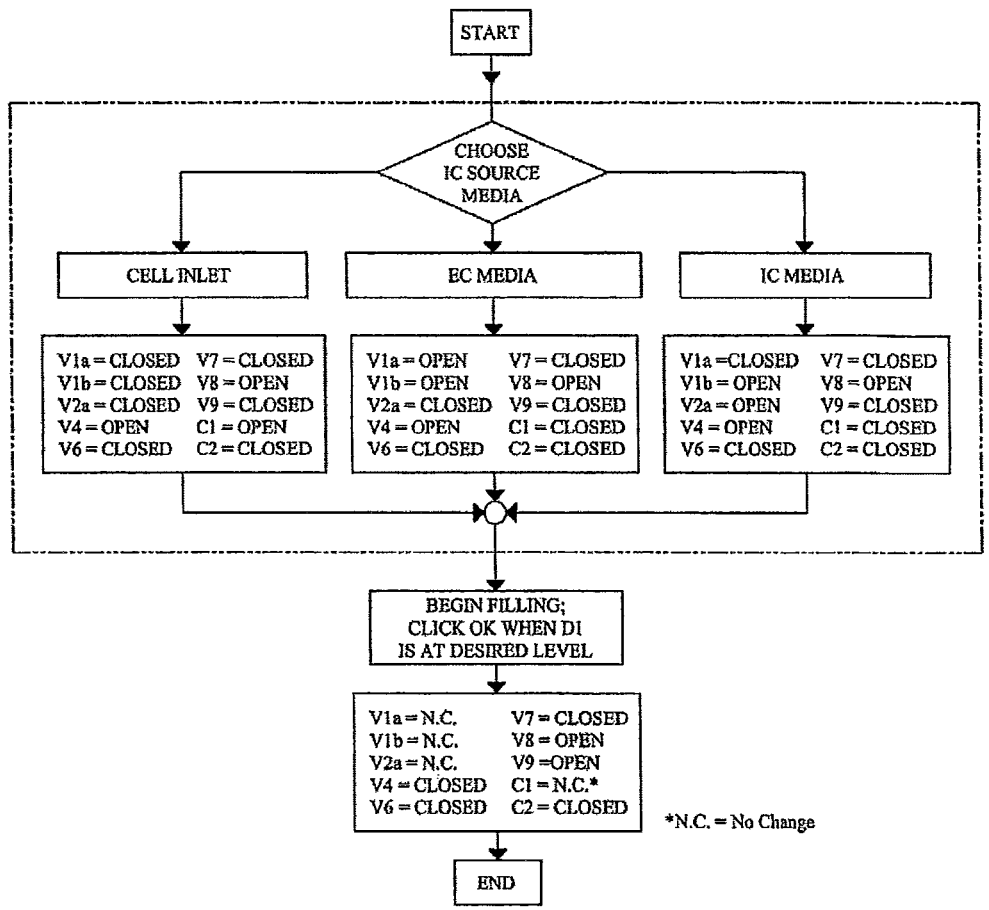
FIG. 8 depicts a flow chart protocol for filling drip chamber D1 in the CES of FIG. 1D.

FIG. 8 depicts a protocol for filling drip chamber D1. Either IC media, EC media, or cells contained in media were added from the IC media bag, EC media bag, or the cell input bag respectively. The valve or clamp separating drip chamber D1 from the bag containing the chosen medium or cell was opened. The medium or cells were then allowed to flow into drip chamber D1. When drip chamber D1 was filled, the valve to the IC media, EC media, or cell input bag was closed.

Figure 9A:
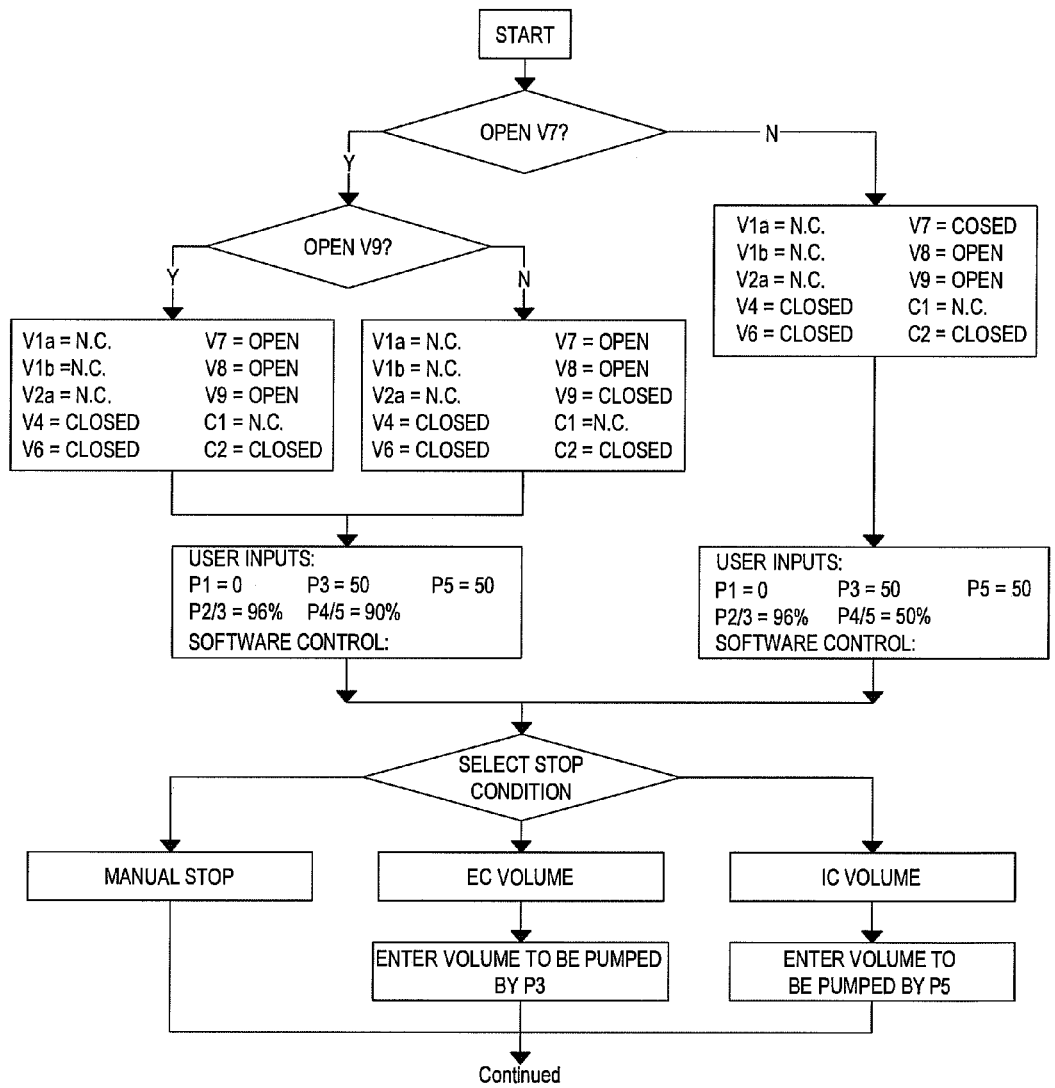
FIGS. 9A and 9B depict a flow chart protocol for exchanging media in the first and second fluid circulation paths in the CES of FIG. 1D.
Figure 9B:
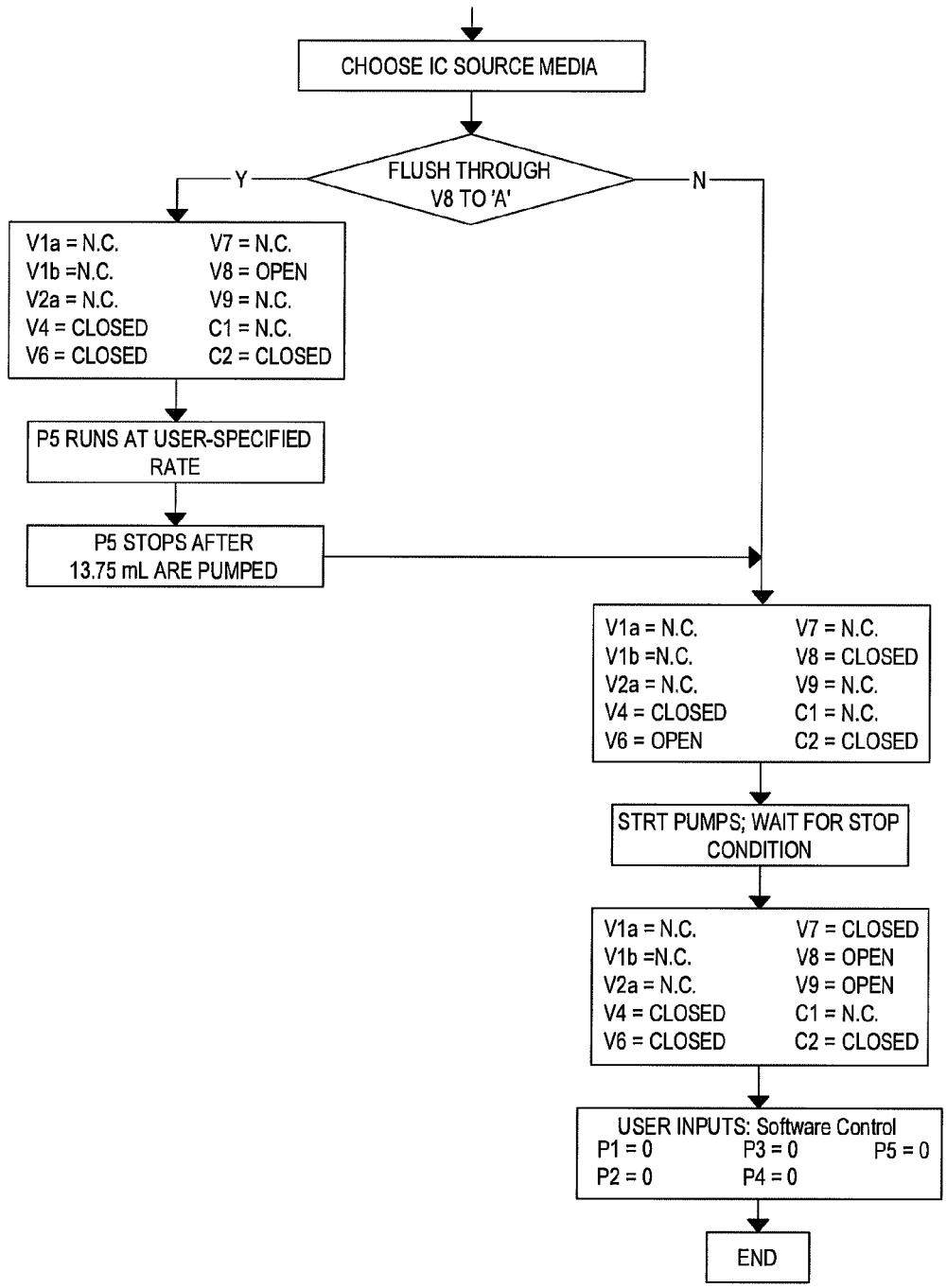

FIGS. 9A and 9B depict a flow diagram protocol for media exchange between EC and IC media in the CES of FIG. 1D. Valve V8, and optionally valves V7 and V9, were opened. IC or EC media was then pumped from drip chamber D1 by pumps P2, P3, P4, and P5. The pump rate ratios of P2/P3 and P4/P5 were selected. Specific IC volumes were pumped into the IC loop by pump P5. Alternatively, specific EC volumes were pumped into the EC loop by pump P3. The new volume of media was flushed from drip chamber D1 by pump P5 through valve V8 to junction A in the IC loop. Alternatively, a specific volume of media (in this case 13.5 mL) was added to the system. The pumps were then turned on, and the media was circulated.

Figure 10:
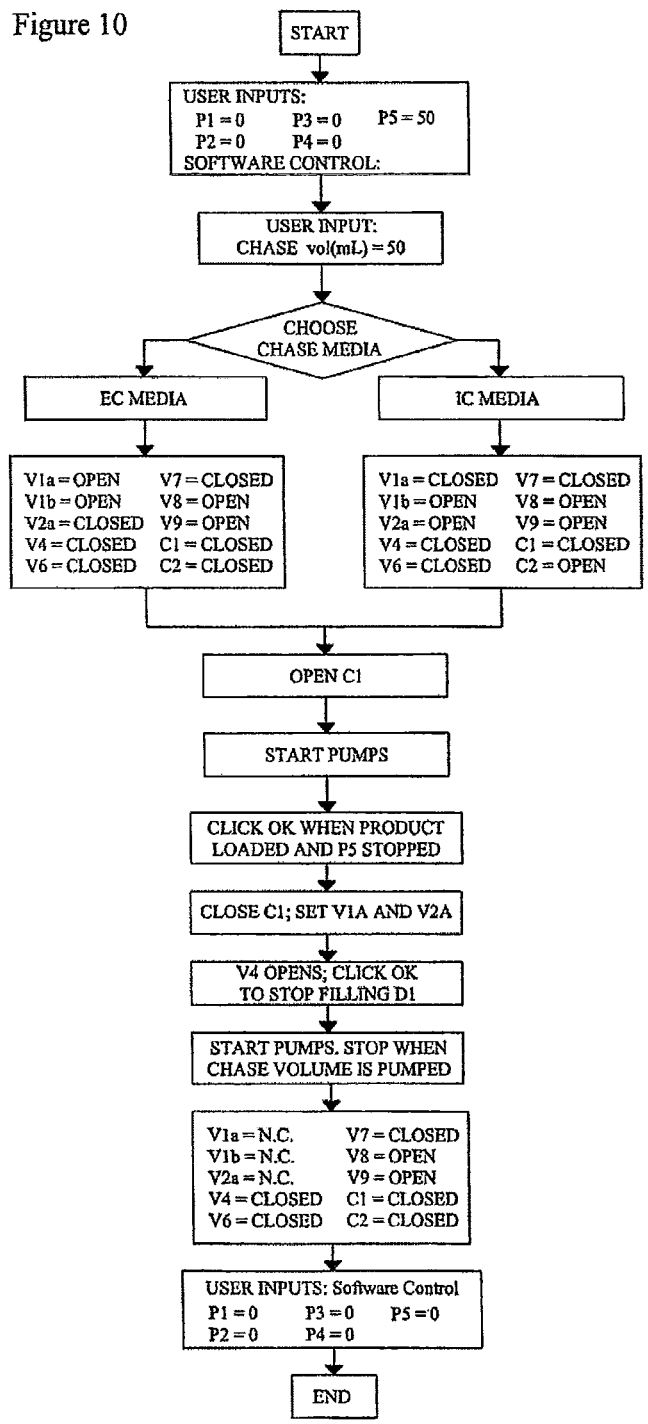
FIG. 10 depicts a flow chart protocol for loading cells into the cell growth chamber of the CES of FIG. 1D.

FIG. 10 depicts a flow diagram protocol for loading cells on the bioreactor by the ultrafiltration method in the CES of FIG. 1D. Clamp C1 was opened, and cells were placed in drip chamber D1. Pump P5 pumped the cells and media from drip chamber D1 into the IC loop. Excess media flowed through the hollow fiber membranes, and departed the system via drip chamber D2. IC or EC chase media were selected, and valves V2a (to IC media bag) or V1b and V1a (to EC media bag) were opened. The pumps are stopped once the chase media was loaded onto the system.

Figure 11:
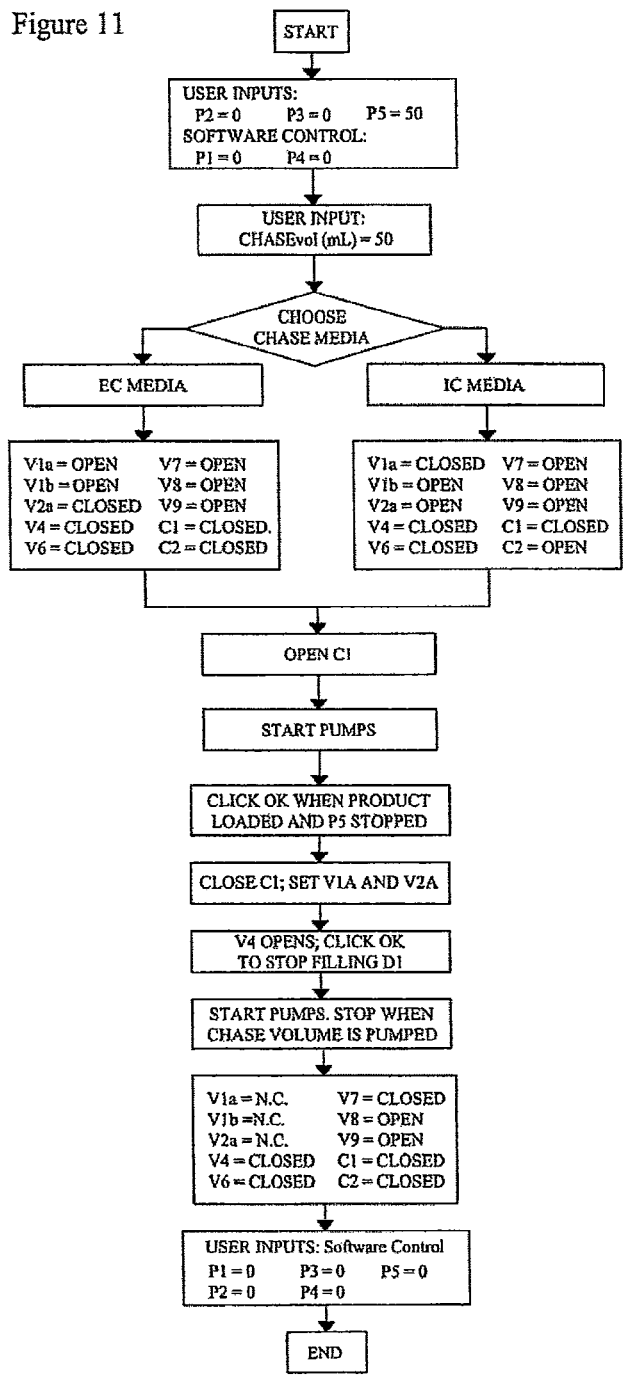
FIG. 11 depicts a flow chart protocol for loading cells into the cell growth chamber of the CES of FIG. 1D.

FIG. 11 depicts a flow diagram protocol for loading cells on the bioreactor by a "passive loading" method. Pump P5 was turned on, IC or EC chase media were selected, and valves V2a (to IC media bag) or V1b and V1a (to EC media bag) were opened. Clamp C1 to cell input bag was opened. Pump P5 pumped at a slow rate to pump cells and associated media from drip chamber D1 to the bioreactor. Excess media flowed out of the IC loop via valve V7 to drip chamber D2. Subsequently, chase IC or EC media was loaded onto the system, and excess media flowed out of the IC loop through valve V5.

Figure 12:
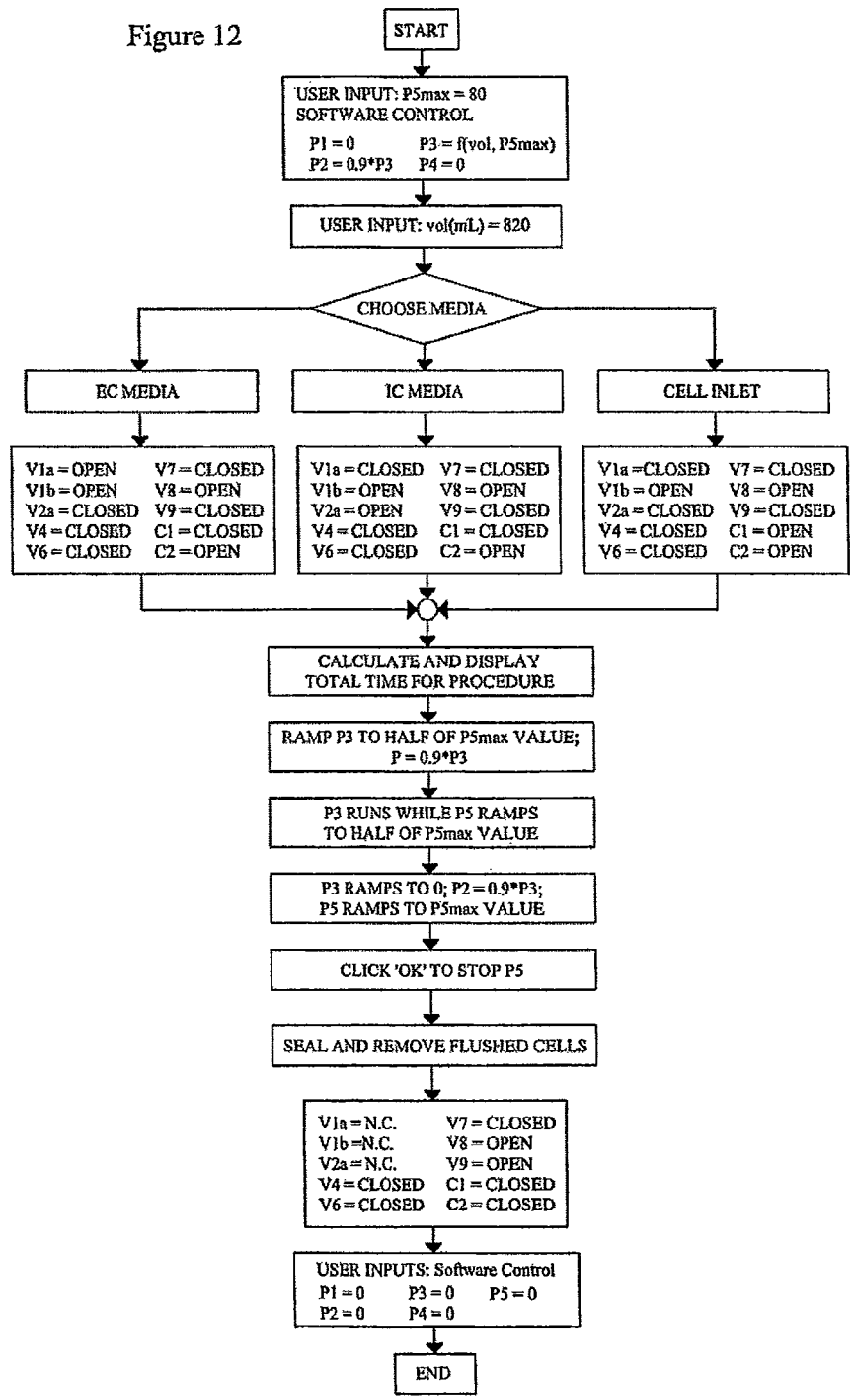
FIG. 12 depicts a flow chart protocol for loading bone marrow cells onto the CES of FIG. 1D.

FIG. 12 depicts a flow diagram protocol for a bone marrow washout in the CES of FIG. 1D. The pressure of pump P5 was set at a high flow rate, and pumps P2 and P3 were set at low flow rates relative to P5. Media from the cell input bag, IC media bag, or EC media bag was then added to drip chamber D1. Cell harvest bag was opened by releasing clamp C2. Pumps P2, P3, and P5 pumped cells and associated media into the cell harvest bag. The cell harvest bag was sealed and removed, and V8 and V9 were reopened.

Figure 13:
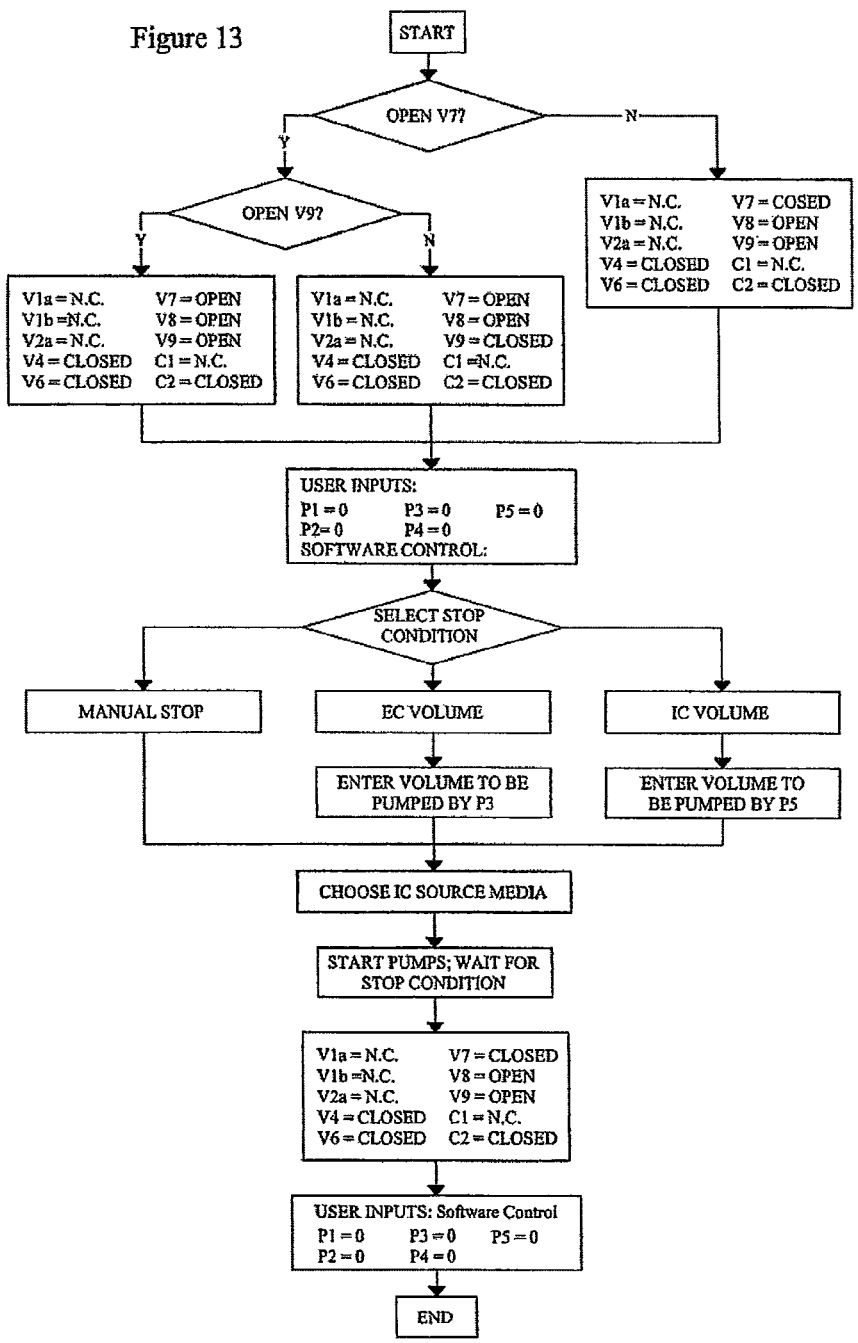
FIG. 13 depicts a flow chart protocol for growing cells in the CES of FIG. 1D.

FIG. 13 depicts a flow diagram protocol for growing adherent cells in the CES of FIG. 1D. Valve V8, and optionally valves V7 and V9, were opened. IC or EC media was then pumped from drip chamber D1 by pumps P2, P3, P4, and P5. Volumes of IC and EC media were then selected. The IC and EC media were pumped by either P3 or P5 onto the system. Valves V8 and V9 were then opened.

Figure 14:
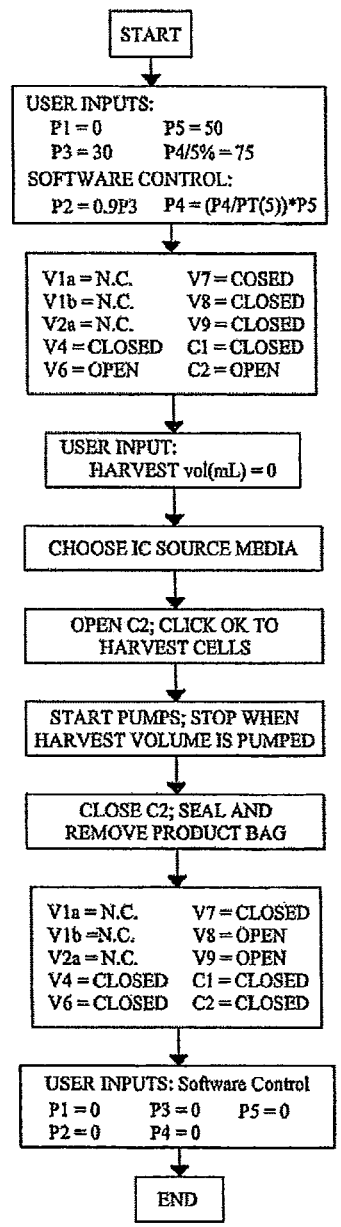
FIG. 14 depicts a flow chart protocol for harvesting cells from the CES of FIG. 1D.

FIG. 14 depicts a flow diagram protocol for harvesting adherent or non-adherent cells from the first circulation path (i.e. the IC loop, including the bioreactor and pump P4) of the CES of FIG. 1D. Pumps P2, P3, P4 and P5 pumped media at selected flow rates. Valve V6 was opened and clamp C2 (to the cell harvest bag) was opened. A harvest volume was selected, and pumps were started for the period of time necessary to pump cells to the harvest bag. Clamp C2 was closed, and the cell harvest bag was removed.

Figure 15:
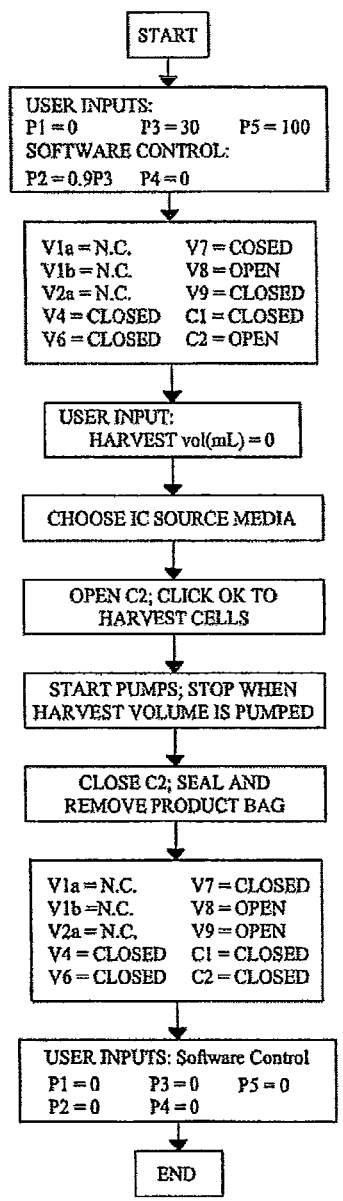
FIG. 15 depicts a flow chart protocol for harvesting cells from the CES of FIG. 1D.

FIG. 15 depicts a flow diagram protocol for harvesting cells adhered to the bioreactor in the CES of FIG. 1D. Pumps P2, P3 and P5 were selected at relative flow rates. Valve V8 was opened and clamp C2 (to the cell harvest bag) was opened. A harvest volume was selected, and pumps were started for the period of time necessary to pump the harvest volume. Clamp C2 was closed, and the cell harvest bag was removed.

Figure 16:
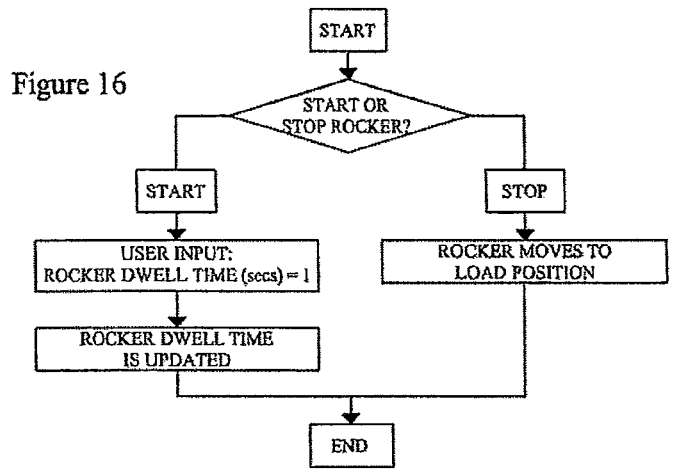
FIG. 16 depicts a flow chart protocol for rocking the cell growth chamber of the CES of FIG. 1D.

FIG. 16 depicts a flow diagram protocol for controlling a rocker attaching the bioreactor in the CES of FIG. 1D. The rocker rotated the bioreactor for a pre-selected period of time, and/or can be set for a pre-selected "dwell time."

Figure 17:
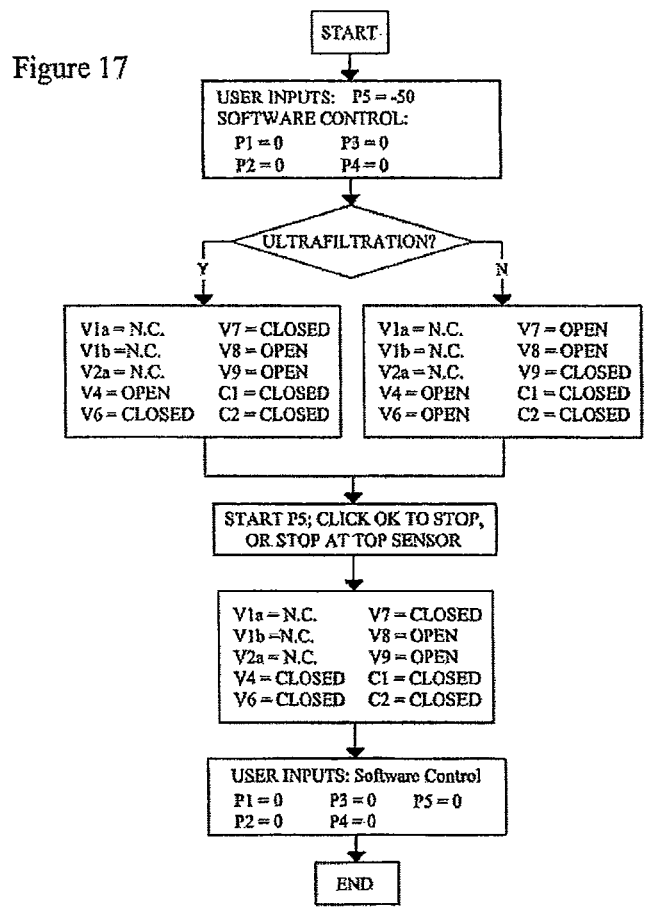
FIG. 17 depicts a flow chart protocol for removing gas from the cell growth chamber of the CES of FIG. 1D.
Figure 18A:
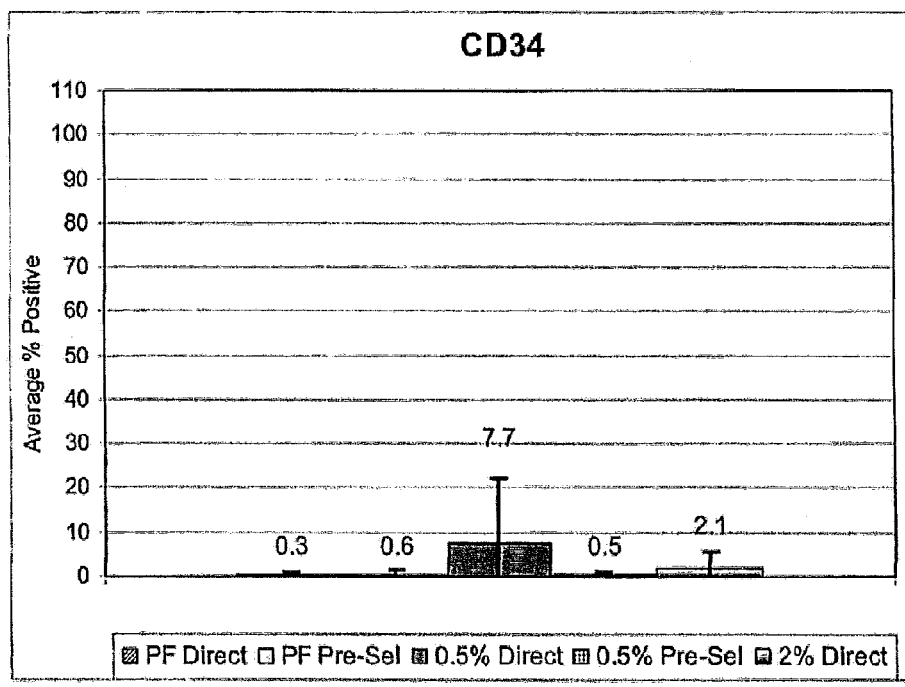
FIGS. 18A, 18B, 18C, 18D, 18E, and 18F depict the expression levels of cell surface markers tested for using different cell growth protocols for cells grown in a hollow fiber bioreactor in the CES of FIG. 1D.
Figure 18B:
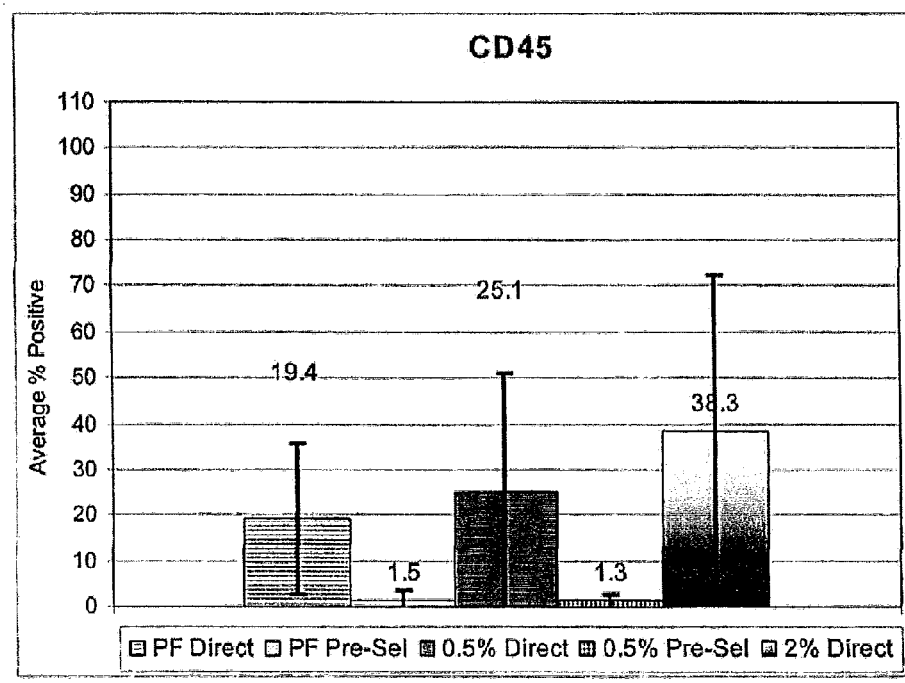
Figure 18C:
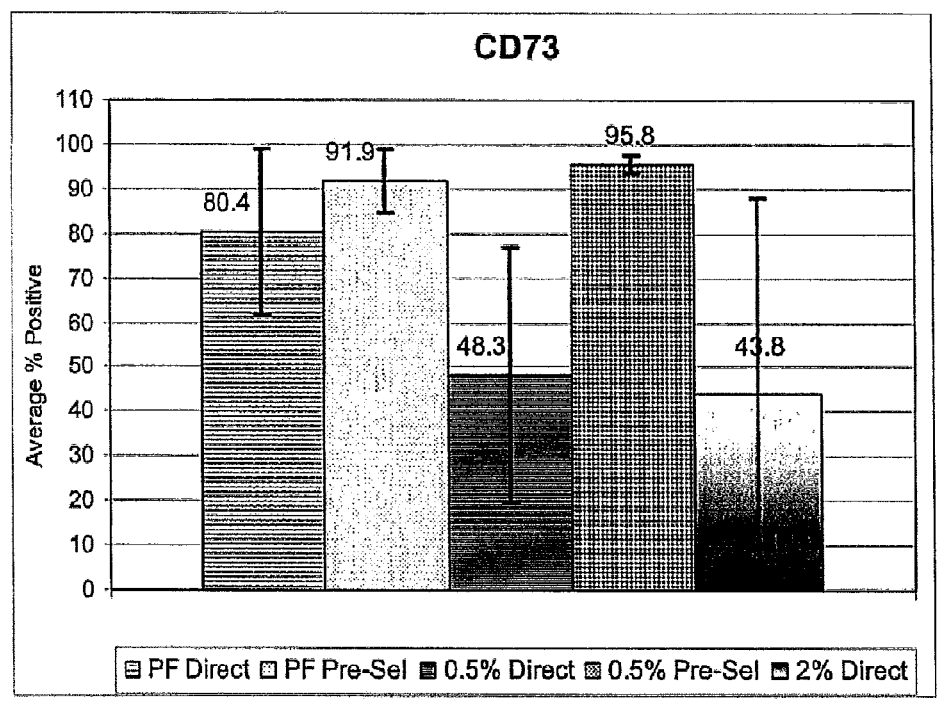
Figure 18D:
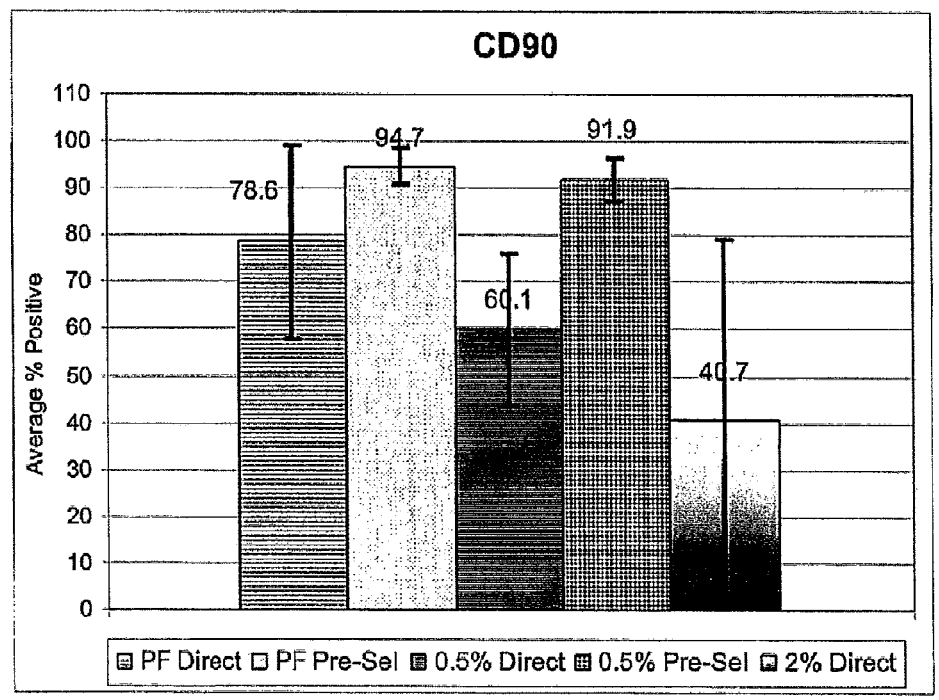
Figure 18E:
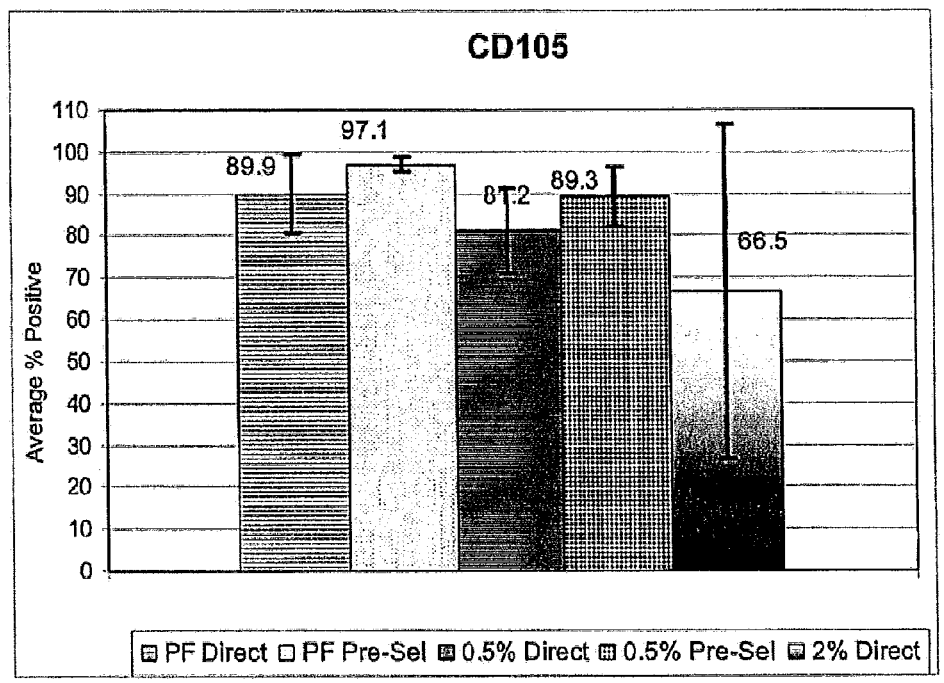
Figure 18F:
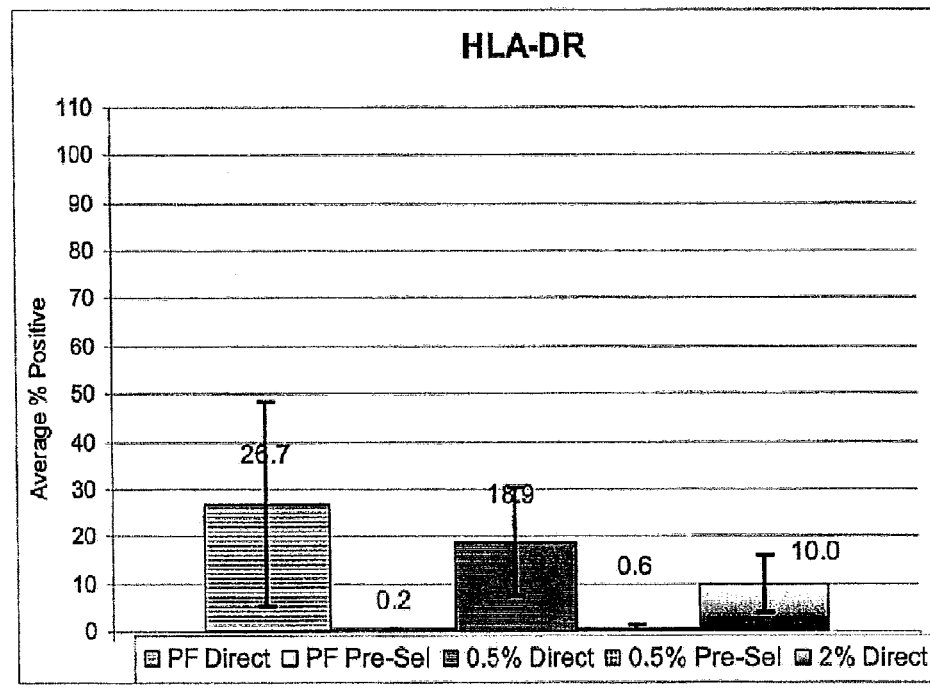

FIG. 17 depicts a flow diagram protocol for removing air from the CES of FIG. 1D. Pump P5 was started in reverse, and media flows through the hollow fibers by ultrafiltration or through the bioreactor via valve V7. Media was collected in drip chamber D1.

Example 6

The initial adhesion and growth rate of mesenchymal stem cells (MSCs) in a hollow fiber cell growth chamber was studied using two sources of MSCs.

The recovery of MSCs from fresh bone marrow collected after 2 days of growth was measured to estimate the number of cells remaining in the cell growth chamber after trypsinization and harvest. Cells remaining in the cell growth chamber were lysed and the LDH mass was measured. LDH mass was compared to a standard LDH per MSC lysed) to estimate the maximum number of MSCs left in the cell growth chamber. This method gave an approximation of the number of MSCs remaining in the cell growth chamber.

Cells were counted using an automated cell counter. Cell viability was determined by dye (trypan blue or erythrosine B) exclusion assay or on an automated counter with viability measurement capabilities. The phenotype of the cells was detected in post-CES harvest, single color flow cytometric determination using CD34, CD45, CD90, CD105, CD73, and HLA-DR with respective isotype control on a FACS flow cytometer. Cell morphology of cells was determined post-harvest. 5,000 cells/cm$^2$ were seeded in 24-well plates (n=3). The morphology of the cells was observed on day 1 after adhesion and 4 days later.

A four-site randomized study testing three cell growth chambers and two MSC sources was conducted. The three cell growth chambers were tested: 1) a 1.7 m$^2$ PA/PAES/PVP membrane, 2) a 1 m$^2$ 0.5% Desmopan membrane, and 3) a 1 m$^2$ 2% Desmopan membrane. The two MSC sources were a) direct seeding of bone marrow (to be tested on all three cell growth chambers) and b) pre-selected plastic adherent MSCs from bone marrow (to be tested only on the first two cell growth chambers).

The study design observed the early attachment and growth of the MSCs, and particularly the initial seeding, attachment, and growth in the cell growth chamber. The measured elements included:
1. Initial MSC binding efficiency.
2. MSC doubling time ($\alpha$).
3. Assuming constant $\alpha$ and initial MSC binding, the projected number of days to a therapeutic dose.
4. Quality of the MSCs, specifically purity, phenotype, and MSC differentiation.

The hollow fiber membrane and MSC source options are shown in Table 1. The 2% Desmopan membrane was tested only with direct seeded bone marrow (i.e. bone marrow that had not been previously selected for MSCs). The other membranes were tested with both direct seeded bone marrow and with pre-selected adherent (T-75) MSCs from bone marrow.

TABLE 1

| Site | Experiment |
|---|---|
| Test Site 4 | 2% Desmopan (direct seed) |
| | 0.5% Desmopan (direct seed and T75) |
| | Fnx2 PA/PAES/PVP (direct seed and T75) |
| Test Site 3 | 2% Desmopan (direct seed) |
| | 0.5% Desmopan (direct seed and T75) |
| | Fnx2 PA/PAES/PVP (direct seed and T75) |
| Test Site 2 | 2% Desmopan (direct seed) |
| | 0.5% Desmopan (direct seed and T75) |
| | Fnx2 PA/PAES/PVP (direct seed and T75) |
| Test Site 1 | 2% Desmopan (direct seed) |
| | 0.5% Desmopan (direct seed and T75) |
| | Fnx2 PA/PAES/PVP (direct seed and T75) |

The CES depicted in FIG. 1B was used for the study. The incubator enclosing the CES was set at 38° C. Table 2 depicts the protocol that was followed for each cell growth chamber. The protocol was identical at each test site.

TABLE 2

Protocol Summary

| Day | 2% Desmopan Direct Seeding | 0.5% Desmopan Direct Seeding | 0.5% Desmopan T75 seeding | Fnx2 PA/PAES/PVP Direct Seeding | Fnx2 PA/PAES/PVP T75 Seeding |
|---|---|---|---|---|---|
| −1 | | | | Fibronectin coated PA/PAES/PVP - 2xFn | |
| 0 | Load ~30 mL bone marrow. | Load ~30 mL bone marrow. | Plate two T75 flasks. | Load ~50 mL bone marrow. | Plate two T75 flasks. |
| 2 | Wash and feed CES | Wash and feed CES | Wash and feed T75 | Wash and feed CES | Wash and feed T-75 |
| 5 | Wash and feed CES | Wash and feed CES | Wash and feed T75 | Wash and feed CES | Wash and feed T-75 |
| 8 | Wash and feed CES | Wash and feed CES | Wash and feed T75 | Wash and feed CES | Wash and feed T-75 |
| 11 | Wash and feed CES | Wash and feed CES | Wash and feed T75 | Wash and feed CES | Wash and feed T-75 |
| 13 | Harvest and count | Harvest and count | | Harvest and count | Fibronectin coat PA/PAES/PVP - 2xFn |
| 14 | | | Harvest T75 and load into CES | | Harvest T75 and load into CES |
| 17 | | | Wash and feed CES | | Wash and feed CES |
| 19 | | | Wash and feed CES | | Wash and feed CES |
| 21 | | | Harvest and count | | Harvest and count |

Table 3 shows data for MSCs prepared in a T-25 flask. The Test Site 3 bone marrow products were collected at Test Site 3 and used in the CES on Day 0. Test Site 4 bone marrow products were collected by Test Site 3 and shipped overnight to Test Site 4 where they were used in the CES on Day 1. Both Test Site 1 and Test Site 2 used commercially purchased bone marrow products shipped overnight and used in the CES on Day 1.

On the day of use in the CES, two 78 μL samples of bone marrow product was plated respectively in two T-25 flasks. The number of observable colonies, total MSCs, and MSC viability were measured seven days after plating.

To understand the effect of overnight storage, the data was measured on both pre-expansion days (specifically by Test Site 3 on bone marrow products sent to Test Site 4) and on post-run days (specifically post runs which did not use the entire 50 mL bone marrow products, i.e. the 1 m² Desmopan cell growth chambers).

The protocol defined that for each cell growth chamber to be seeded with adherent pre-selected MSCs, two T-75 flasks would be plated with 3×78 μL (234 μL) of bone marrow. Fourteen days after plating, both T-75 flasks were harvested using standard trypsin techniques. One harvest was used to seed the cell growth chamber and the second harvest was counted. (To reduce the possibility of contamination during open events, the samples were not mixed and then divided.)

TABLE 3

T-25 Cell Count Data

T25 Flask Data

| | | | Days post collection | | | | | | | |
|---|---|---|---|---|---|---|---|---|---|---|
| | | | 0 | | | 1 | | | 2 | | |
| | | Sample # | # Colonies | MSC Count | Viability (%) | # Colonies | MSC Count | Viability (%) | # Colonies | MSC Count | Viability (%) |
| 2% Desmopan | Test Site 1 | A | | | | 19 | 27600 | 80.2 | 19 | 48000 | 89.6 |
| | | B | | | | 14 | 28500 | 82.8 | 17 | 55000 | 91.5 |
| | Test Site 2 | A | | | | 13 | 24000 | 95.0 | | | |
| | | B | | | | 11 | 13000 | 98.0 | | | |
| | Test Site 3 | A | 150 | 140000 | 100.0 | 106 | 115000 | 100.0 | 108 | 8310 | 100.0 |
| | | B | 150 | 230000 | 100.0 | 140 | 140000 | 100.0 | 124 | 9450 | 100.0 |
| | Test Site 4 | A | 111 | | | 74 | 17420 | 95.0 | 63 | 21780 | 95.0 |
| | | B | 86 | | | 73 | 17790 | 95.0 | 91 | 33540 | 95.0 |
| 0.5% Desmopan | Test Site 1 | A | | | | 29 | 38000 | 93.4 | 19 | 15300 | 89.3 |
| | | B | | | | 34 | 39300 | 96.1 | 16 | 17600 | 85.9 |
| | Test Site 2 | A | | | | 56 | 222000 | 88.3 | 33 | 19500 | 56.0 |
| | | B | | | | 50 | 149000 | 80.9 | 25 | 28000 | 73.4 |
| | Test Site 3 | A | 83 | 4950 | 100.0 | 46 | 1870 | 100.0 | 64 | 2400 | 100.0 |
| | | B | 70 | 4500 | 100.0 | 47 | 1870 | 100.0 | 67 | 2550 | 100.0 |
| | Test Site 4 | A | 16 | 310 | | 1 | 60 | 95.0 | | | |
| | | B | 7 | 140 | | 2 | 34 | 95.0 | | | |
| PA/PAES/PVP | Test Site 1 | A | | | | 56 | 55000 | 94.5 | | | |
| | | B | | | | 48 | 36600 | 88.7 | | | |
| | Test Site 2 | A | | | | 25 | 360000 | 87.0 | | | |
| | | B | | | | 29 | 280000 | 88.0 | | | |
| | Test Site 3 | A | 32 | 1350 | 100.0 | | | | | | |
| | | B | 43 | 1680 | 100.0 | | | | | | |
| | Test Site 4 | A | 185 | | | 127 | 16710 | 95.0 | | | |
| | | B | 184 | | | 160 | 166 30 | 95.0 | | | |

These data are shown in Table 4.

TABLE 4

| | | T75 Flasks | | Directly Seeded Cell growth chamber | | | Cell growth chamber with pre-selected MSCs (flask grown) | | |
|---|---|---|---|---|---|---|---|---|---|
| | | MSC Count on day 14 | Viability (%) | MSC Count Day 13 | Viability (%) | LDH Results (Calc # of Cells) | MSC Count Day 7 | Viability (%) | LDH Results (Calc # of Cells) |
| 2% Desmopan | Test Site 1 | | | 1.08E+07 | 93.0 | 2.97E+05 | | | |
| | Test Site 2 | | | 4.37E+06 | 50.8 | <DL | | | |
| | Test Site 3 | | | 6.30E+06 | 73.0 | 2.35E+05 | | | |
| | Test Site 4 | | | 3.41E+06 | 97.2 | 2.31E+05 | | | |
| 0.5% Desmopan | Test Site 1 | 2.86E+06 | 95.3 | 1.01E+07 | 87.9 | 1.67E+06 | 1.04E+07 | 91.2 | 2.93E+05 |
| | Test Site 2 | 4.22E+06 | 90.0 | 1.38E+07 | 35.9 | | 4.75E+06 | 95.0 | |
| | Test Site 3 | 1.43E+06 | 100.0 | 6.23E+06 | 91.1 | 3.75E+05 | 4.20E+06 | 92.1 | <DL |
| | Test Site 4 | 7.05E+05 | 95.1 | 1.62E+06 | | 9.47E+05 | 1.05E+06 | 96.9 | 3.47E+04 |

TABLE 4-continued

|  |  | T75 Flasks | | Directly Seeded Cell growth chamber | | | Cell growth chamber with pre-selected MSCs (flask grown) | | |
|---|---|---|---|---|---|---|---|---|---|
|  |  | MSC Count on day 14 | Viability (%) | MSC Count Day 13 | Viability (%) | LDH Results (Calc # of Cells) | MSC Count Day 7 | Viability (%) | LDH Results (Calc # of Cells) |
| PA/PAES/ PVP | Test Site 1 | 3.93E+06 | 97.5 | 3.45E+07 | 92.3 | 3.10E+06 | 6.50E+07 | 88.9 | 0.00E+00 |
|  | Test Site 2 | 1.50E+06 | 84.0 | 8.00E+06 | 66.5 |  | 9.25E+07 | 93.8 |  |
|  | Test Site 3 | 8.50E+05 | 100.0 | 1.58E+07 | 90.5 | 2.12E+06 | 1.87E+07 | 92.0 | <DL |
|  | Test Site 4 | 4.87E+06 | 94.9 | 6.32E+07 | 98.2 | 1.33E+06 | 5.83E+07 | 98.2 | 1.16E+06 |

Where DL is the assay detection limit.
DL for Test Site 3 = 5.4E+04

Table 4 depicts MSC count data for T-75 flasks, Directly Seeded Cell growth chambers, and Cell growth chambers with Pre-Selected MSCs. Table 4 also shows the count data for the direct seeded cell growth chamber harvests and the count data for the cell growth chamber harvests with pre-selected MSCs. All directly seeded cell growth chambers were able to produce viable MSCs, though Test Site 2 produced lower quantities of MSCs. A lower quantity of cells was measured at Test sites 1 and 4 using the 0.5% desmopan as compared to the T75 flask preparation method. However, all cells had high viability. Test site 4 produced a comparable quantity of highly viable MSCs as compared to the T75 flasks.

Various stem cell markers were used to detect stem cells in each of the 2% Desmopan, 0.5% Desmopan, and PA/PAES/PVP hollow fiber membranes. Tables 5, 6, and 7 show phenotype data for the harvests.

TABLE 5

0.5% Desmopan

| | | | % Positive | | | |
|---|---|---|---|---|---|---|
| Site | CD34 | CD45 | CD73 | CD90 | CD105 | HLA-DR |
| Directly Seeded Bioreactor | | | | | | |
| Test Site 1 | 0.8 | 25.0 | 70.2 | 72.0 | 91.8 | 28.5 |
| Test Site 2 | 29.5 | 61.0 | 18.3 | | | |
| Test Site 3 | 0.0 | 14.3 | 75.1 | 66.3 | 79.6 | 6.4 |
| Test Site 4 | 0.4 | 0.2 | 29.7 | 41.9 | 72.1 | 21.9 |
| Average: | 7.7 | 25.1 | 48.3 | 60.1 | 81.2 | 18.9 |
| Standard Dev: | 14.6 | 26.0 | 28.5 | 16.0 | 9.9 | 11.3 |
| Bioreactor with Pre-Selected MSCs | | | | | | |
| Test Site 1 | 0.5 | 0.3 | 96.3 | 97.7 | 95.7 | 0.5 |
| Test Site 2 | 1.3 | 3.6 | 97.6 | 87.9 | 91.7 | 1.2 |
| Test Site 3 | 0.0 | 0.0 | 93.6 | 90.3 | 80.5 | 0.0 |
| Test Site 4 | 0.2 | 1.6 | 97.5 | 94.6 | 82.6 | 1.4 |
| Average: | 0.5 | 1.3 | 95.8 | 91.9 | 89.3 | 0.6 |
| Standard Dev: | 0.6 | 1.6 | 1.9 | 4.4 | 7.3 | 0.7 |

TABLE 6

Phenotype data for 0.5% Desmopan harvests.
2% Desmopan
Directly Seeded Bioreactor

| | | | % Positive | | | |
|---|---|---|---|---|---|---|
| Site | CD34 | CD45 | CD73 | CD90 | CD105 | HLA-DR |
| Test Site 1 | 0.5 | 87.6 | 2.3 | 0.3 | 78.4 | 10.8 |
| Test Site 2 | 7.8 | 33.9 | 9.0 | 15.0 | 7.5 | 17.8 |
| Test Site 3 | 0.0 | 13.8 | 81.7 | 76.5 | 85.4 | 3.9 |
| Test Site 4 | 0.1 | 17.8 | 82.2 | 71.0 | 94.6 | 7.4 |

TABLE 6-continued

Phenotype data for 0.5% Desmopan harvests.
2% Desmopan
Directly Seeded Bioreactor

| | | | % Positive | | | |
|---|---|---|---|---|---|---|
| Site | CD34 | CD45 | CD73 | CD90 | CD105 | HLA-DR |
| Average: | 2.1 | 38.3 | 43.8 | 40.7 | 66.5 | 10.0 |
| Standard Dev: | 3.8 | 34.0 | 44.1 | 38.7 | 39.9 | 5.9 |

TABLE 7

Phenotype data for PA/PAES/PVP Membrane harvests.
Fnx2 PA/PAES/PVP

| | | | % Positive | | | |
|---|---|---|---|---|---|---|
| Site | CD34 | CD45 | CD73 | CD90 | CD105 | HLA-DR |
| Directly Seeded Bioreactor | | | | | | |
| Test Site 1 | 0.3 | 12.0 | 90.8 | 85.8 | 91.3 | 6.4 |
| Test Site 2 | 1.0 | 7.8 | 93.6 | 98.8 | 97.0 | 17.9 |
| Test Site 3 | 0.0 | 43.9 | 53.1 | 50.2 | 76.5 | 25.8 |
| Test Site 4 | 0.1 | 14.0 | 84.3 | 79.7 | 95.1 | 56.6 |
| Average: | 0.3 | 19.4 | 80.4 | 78.6 | 89.9 | 26.7 |
| Standard Dev: | 0.5 | 16.5 | 18.6 | 20.6 | 9.3 | 21.5 |
| Bioreactor with Pre-Selected MSCs | | | | | | |
| Test Site 1 | 0.1 | 0.2 | 98.5 | 99.3 | 96.2 | 0.5 |
| Test Site 2 | 2.1 | 4.1 | 83.8 | 92.0 | 99.7 | 0.2 |
| Test Site 3 | 0.0 | 0.0 | 93.4 | 92.9 | 95.4 | 0.0 |
| Test Site 4 | 0.1 | 0.1 | 99.6 | 99.3 | 97.5 | 0.2 |
| Average: | 0.6 | 1.5 | 91.9 | 94.7 | 97.1 | 0.2 |
| Standard Dev: | 1.0 | 2.0 | 7.2 | 4.0 | 1.9 | 0.2 |

Figure 3:
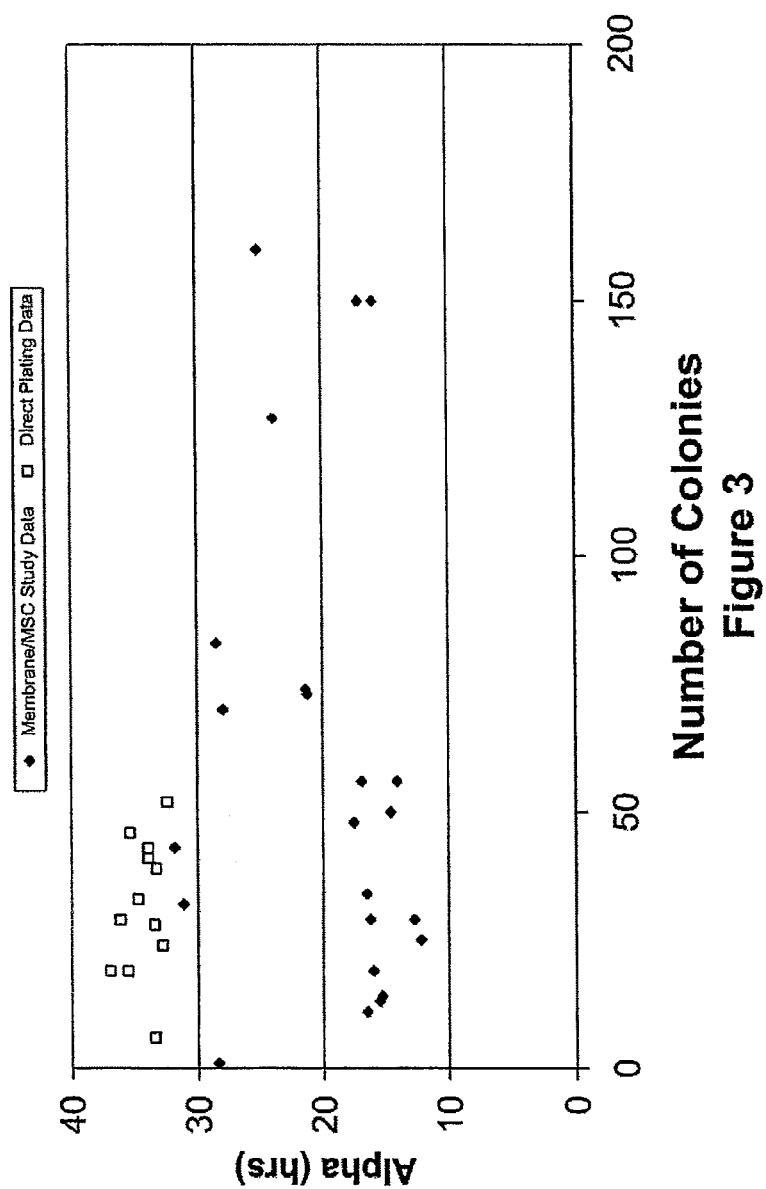
FIG. 3 depicts the mesenchymal stem cells (MSC) doubling time (a) as a function of the number of colonies in flask prepared samples of MSCs.
Figure 6A:
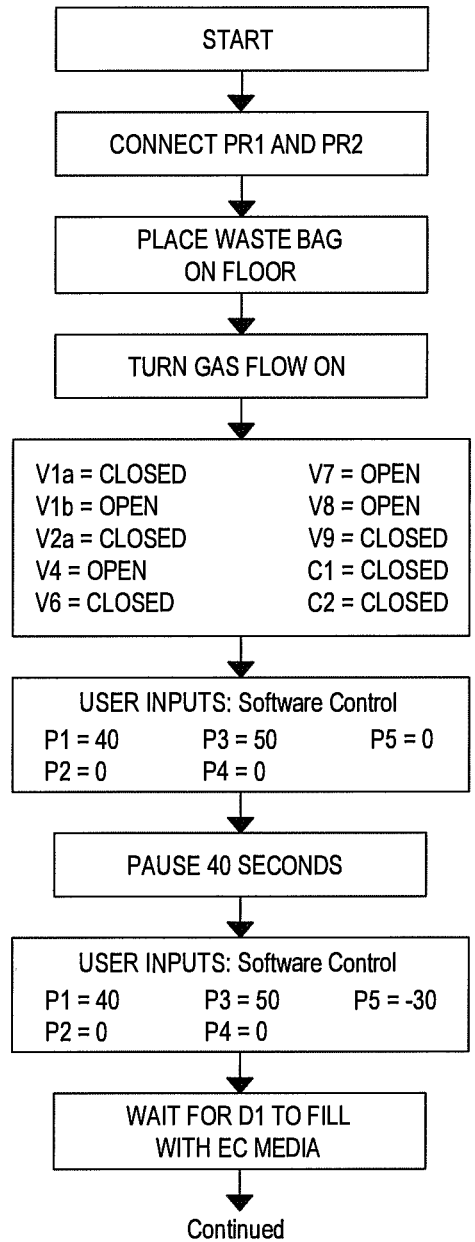
FIGS. 6A, 6B, 6C, and 6D depict a flow chart protocol for priming the CES of FIG. 1D.
Figure 6B:
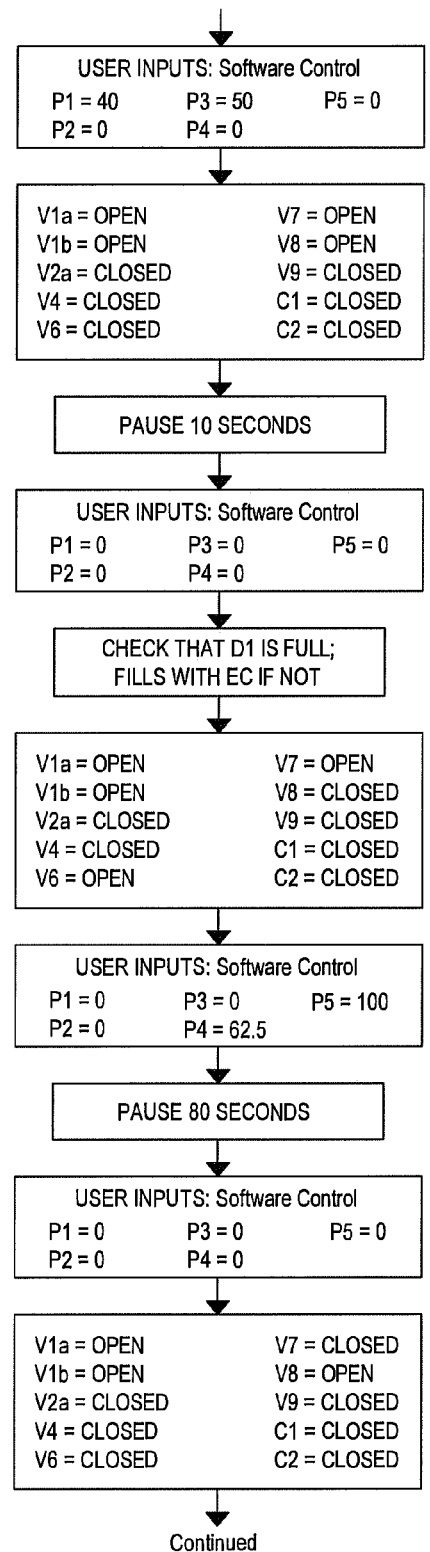
Figure 6C:
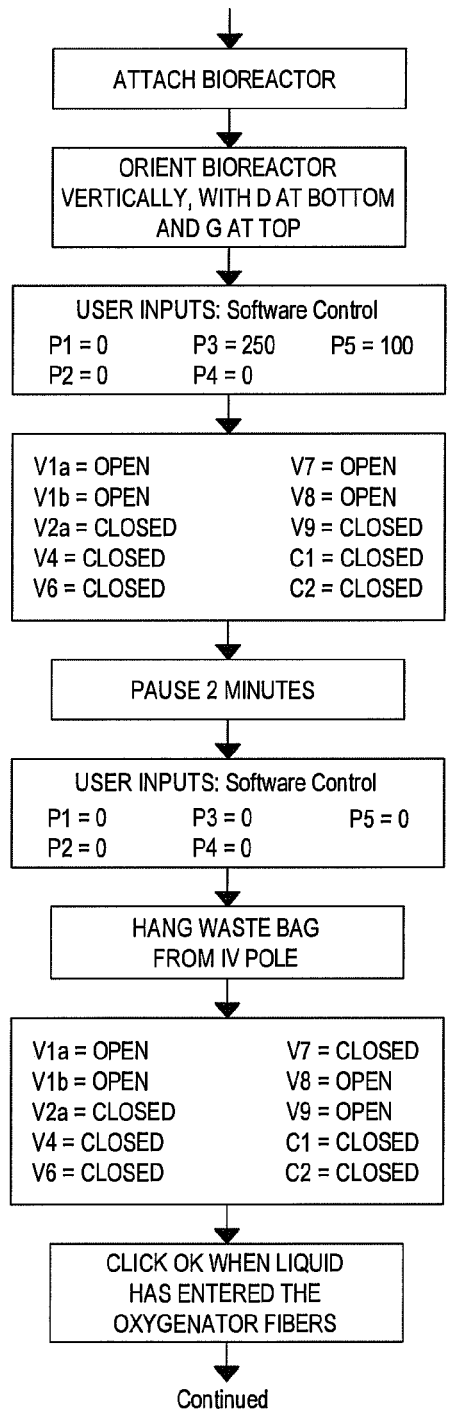
Figure 6D:
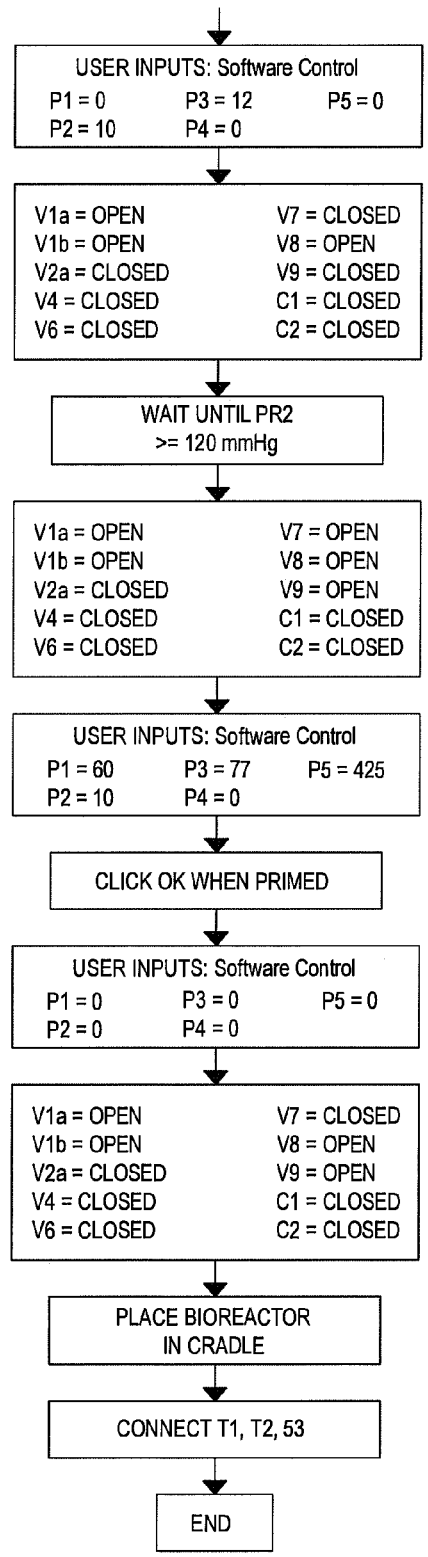

Table 8 shows the calculated MSC doubling times ($\alpha$, alpha) for the T-25 flask data. Also included in this table is the T-25 flask data using 78 μL of bone marrow collected during a direct plating stem cell study. These data are plotted in FIG. 3.

For bone marrow products which yield around 50 colony forming units (CFUs) or less, the data is clustered in two groups. With the exception that a majority of those data with the higher alpha are from Test Site 3, whereas those data from the lower group are predominately from sites other than Test Site 3, no common characteristic is obvious.

The T-25 flask data showing the effect of bone marrow age on both CFUs and on the MSC doubling time is graphed in FIG. 4 and FIG. 5, respectively. These data correspond to plating 78 μL of bone marrow and counting the CFUs and total MSCs seven days later.

FIGS. 18A, 18B, 18C, 18D, 18E, and 18F depict the expression levels of cell surface markers tested for using different cell growth protocols for cells grown in a hollow fiber bioreactor in the CES of FIG. 1D. "Direct" refers to cells loaded directly on the bioreactor. "Pre-sel" refers to cells grown in a flask and pre-selected for MSC characteristics that are then grown using a hollow fiber bioreactor. 0.5% refers to cells grown on hollow fiber bioreactors loaded with 0.5% Desmopan. 2% refers to cells grown in bioreactors loaded with 2% Desmopan. PA/PAES/PVP refers to cells grown using a PA/PAES/PVP hollow fiber bioreactor.

TABLE 8

Calculation of Alpha for T-25 flask.

| | | | D | E | F | G | H | I |
|---|---|---|---|---|---|---|---|---|
| | | | | | T25 Flask Data | | | |
| | | | T25 Flask day 7 Data 0.078 ml from 50 ml Bone Marrow Aspirate | | | | | |
| | | | # Colonies | MSC Count | Δt (days) | α (hrs) | Average # colonies | Average α (hrs) |
| 2% Desmopan | Test Site 1 | A | 19 | 2.76E+04 | 7 | 16.0 | 16.5 | 15.6 |
| | | B | 14 | 2.85E+04 | 7 | 15.3 | | |
| | Test Site 2 | A | 13 | 2.40E+04 | 7 | 15.5 | 12.0 | 16.0 |
| | | B | 11 | 1.30E+04 | 7 | 16.5 | | |
| | Test Site 3 | A | 150 | 1.40E+05 | 7 | 17.0 | 150.0 | 16.5 |
| | | B | 150 | 2.30E+05 | 7 | 15.9 | | |
| | Test Site 4 | A | 74 | 1.74E+04 | 7 | 21.3 | 73.5 | 21.3 |
| | | B | 73 | 1.78E+04 | 7 | 21.2 | | |
| 0.5% Desmopan | Test Site 1 | A | 29 | 3.80E+04 | 7 | 16.2 | 31.5 | 16.4 |
| | | B | 34 | 3.93E+04 | 7 | 16.5 | | |
| | Test Site 2 | A | 56 | 2.22E+05 | 7 | 14.1 | 53.0 | 14.3 |
| | | B | 50 | 1.49E+05 | 7 | 14.6 | | |
| | Test Site 3 | A | 83 | 4.95E+03 | 7 | 28.5 | 76.5 | 28.2 |
| | | B | 70 | 4.50E+03 | 7 | 28.0 | | |
| | Test Site 4 | A | 1 | 6.00E+01 | 7 | 28.4 | 1.5 | 34.8 |
| | | B | 2 | 3.40E+01 | 7 | 41.1 | | |
| PA/PAES/PVP | Test Site 1 | A | 56 | 5.50E+04 | 7 | 16.9 | 52.0 | 17.2 |
| | | B | 48 | 3.66E+04 | 7 | 17.5 | | |
| | Test Site 2 | A | 25 | 3.60E+05 | 7 | 12.2 | 27.0 | 12.4 |
| | | B | 29 | 2.80E+05 | 7 | 12.7 | | |
| | Test Site 3 | A | 32 | 1.35E+03 | 7 | 31.1 | 37.5 | 31.4 |
| | | B | 43 | 1.68E+03 | 7 | 31.8 | | |
| | Test Site 4 | A | 127 | 1.67E+04 | 7 | 23.9 | 143.5 | 24.5 |
| | | B | 160 | 1.66E+04 | 7 | 25.1 | | |
| | Test Site 3 Direct Seeding Study | A | 19 | 5.03E+02 | 7 | 35.5 | 14.7 | 35.3 |
| | | B | 19 | 4.46E+02 | 7 | 36.9 | | |
| | | C | 6 | 1.97E+02 | 7 | 33.4 | | |
| | | A | 46 | 1.24E+03 | 7 | 35.3 | 45.7 | 33.6 |
| | | B | 39 | 1.30E+03 | 7 | 33.2 | | |
| | | C | 52 | 1.91E+03 | 7 | 32.3 | | |
| | | A | 33 | 9.46E+02 | 7 | 34.7 | 39.0 | 34.2 |
| | | B | 41 | 1.27E+03 | 7 | 33.9 | | |
| | | C | 43 | 1.34E+03 | 7 | 33.9 | | |
| | | A | 24 | 8.40E+02 | 7 | 32.8 | 27.0 | 34.1 |
| | | B | 28 | 9.16E+02 | 7 | 33.4 | | |
| | | C | 29 | 7.30E+02 | 7 | 36.1 | | |

I claim:

1. A detachable flow circuit configured to attach to a fixed portion of a cell expansion system comprising a plurality of controllers, the detachable flow circuit comprising:

a first fluid circulation path comprising a first fluid flow path having at least opposing ends, a first end of the first fluid flow path configured to fluidly associate with a first inlet port of a cell growth chamber and a second opposing end of the first fluid flow path configured to fluidly associate with a first outlet port of the cell growth chamber wherein a portion of the first fluid circulation path is configured to be disposably mounted to a first fluid controller of the fixed portion of the cell expansion system;

a second fluid circulation path comprising a second fluid flow path having at least opposing ends, one end of the second fluid flow path configured to fluidly associate with a second inlet of the cell growth chamber and a second opposing end of the second fluid flow path configured to fluidly associate with a second outlet of the cell growth chamber, wherein a portion of the second fluid circulation path is configured to be disposably mounted to a second fluid controller of the fixed portion of the cell expansion system;

a first fluid inlet path fluidly associated with the first fluid circulation path;

a first fluid outlet path fluidly associated with at least one of the first or second fluid circulation paths;

a first fluid connector path having at least opposing ends, a first opposing end of the first fluid connector path fluidly associated with the first fluid circulation path and a second opposing end of the first fluid connector path fluidly associated with the second fluid circulation path, wherein a portion of the first fluid connector path is configured to be disposably mounted to a third fluid controller of the fixed portion of the cell expansion system; and a second fluid connector path having opposing ends, one end of the second fluid connector path fluidly associated with the first fluid flow path and a second end of the second fluid connector path fluidly associated with the second fluid flow path, wherein a portion of the second fluid connector path is configured to be disposably mounted to a fourth fluid controller of the fixed portion of the cell expansion system.

2. The detachable flow circuit of claim 1, wherein the first fluid controller, the second fluid controller, the third fluid controller, and the fourth fluid controller each are independently selected from the group consisting of: a pump, a valve, clamps, and combinations thereof.

3. The detachable flow circuit of claim 2, wherein the cell growth chamber is configured to allow media in the first fluid flow path to flow in the opposite direction than the second fluid flow path in the cell growth chamber.

4. The detachable flow circuit of claim 1, further comprising:
an oxygenator; and
tubing connecting the oxygenator to the cell growth chamber.

5. The detachable flow circuit of claim 1, further comprising one or more bags, wherein the one or more bags store one or more from the group consisting of: media and cells.

6. The detachable flow circuit of claim 1, wherein the cell growth chamber is configured to be operably attached to a rocker on the fixed portion of the cell expansion system, and wherein the cell growth chamber is rotatable by the rocker around a central axis of said cell growth chamber.

7. The detachable flow circuit of claim 1, wherein the cell growth chamber is configured to be operably attached to a rocker on the fixed portion of the cell expansion system, and wherein the cell growth chamber is rotatable by the rocker around an axis normal to a central axis of said cell growth chamber.

8. The detachable flow circuit of claim 1, wherein fluid in the first fluid circulation path flows through an intracapillary space of one or more hollow fibers in the cell growth chamber.

9. The detachable flow circuit of claim 1, wherein fluid in the second fluid circulation path flows through an extracapillary space of one or more hollow fibers in the cell growth chamber.

* * * * *